(12) United States Patent
Bonnette et al.

(10) Patent No.: US 8,475,487 B2
(45) Date of Patent: Jul. 2, 2013

(54) CROSS STREAM THROMBECTOMY CATHETER WITH FLEXIBLE AND EXPANDABLE CAGE

(75) Inventors: Michael J. Bonnette, Minneapolis, MN (US); Eric J. Thor, Arden Hills, MN (US); Daniel T. Janse, Lino Lakes, MN (US)

(73) Assignee: Medrad, Inc., Indianola, PA (US)

( * ) Notice: Subject to any disclaimer, the term of this patent is extended or adjusted under 35 U.S.C. 154(b) by 1938 days.

(21) Appl. No.: 11/101,224

(22) Filed: Apr. 7, 2005

(65) Prior Publication Data

US 2006/0229645 A1   Oct. 12, 2006

(51) Int. Cl.
  *A61M 29/00*   (2006.01)
  *A61B 17/22*   (2006.01)

(52) U.S. Cl.
  USPC .......................... 606/191; 606/200; 606/127

(58) Field of Classification Search
  USPC .................................................. 606/198, 200
  See application file for complete search history.

(56) References Cited

U.S. PATENT DOCUMENTS

| | | | |
|---|---|---|---|
| 4,950,238 A * | 8/1990 | Sullivan ...................... | 604/22 |
| 4,998,539 A | 3/1991 | Delsanti | |
| 5,370,609 A | 12/1994 | Drasler et al. | |
| 5,423,799 A | 6/1995 | Shiu | |
| 5,490,859 A | 2/1996 | Mische et al. | |
| 5,766,191 A | 6/1998 | Trerotola | |
| 5,785,675 A | 7/1998 | Drasler et al. | |
| 5,795,322 A | 8/1998 | Boudewijn | |
| 5,846,260 A | 12/1998 | Maahs | |
| 5,911,734 A | 6/1999 | Tsugita et al. | |
| 5,941,869 A | 8/1999 | Patterson et al. | |
| 5,941,896 A | 8/1999 | Kerr | |
| 5,947,985 A | 9/1999 | Imran | |
| 5,972,019 A | 10/1999 | Engelson et al. | |
| 6,001,112 A | 12/1999 | Taylor | |
| 6,004,269 A | 12/1999 | Crowley et al. | |
| 6,036,708 A | 3/2000 | Sciver | |

(Continued)

FOREIGN PATENT DOCUMENTS

| WO | 01/74255 A1 | 10/2001 |
|---|---|---|
| WO | WO2006/110186 | 10/2006 |

OTHER PUBLICATIONS

International Search Report issued in corresponding PCT patent application, PCT/US2005/041411.

(Continued)

*Primary Examiner* — Corrine M McDermott
*Assistant Examiner* — Melissa Ryckman
(74) *Attorney, Agent, or Firm* — David Schramm

(57) ABSTRACT

A cross stream thrombectomy catheter with a flexible and expandable cage preferably formed of nitinol for removal of hardened and aged thrombotic material stubbornly attached to the interior of a blood vessel. The cage, which can be mesh or of straight or spiral filament design, is located close to inflow and outflow orifices at the distal portion of a catheter tube and is deployed and extended at a thrombus site for intimate contact therewith and for action of a positionable assembly and subsequent rotation and lineal actuation to abrade, grate, scrape, or otherwise loosen and dislodge difficult to remove thrombus which can interact with cross stream flows to exhaust free and loosened thrombotic particulate through the catheter tube. An alternative embodiment discloses a mechanism involving a threaded tube in rotatable engagement with an internally threaded sleeve to incrementally control the deployment and expansion of the flexible and expandable cages.

39 Claims, 20 Drawing Sheets

U.S. PATENT DOCUMENTS

| | | | |
|---|---|---|---|
| 6,096,001 | A | 8/2000 | Drasler et al. |
| 6,129,697 | A | 10/2000 | Drasler et al. |
| 6,156,046 | A | 12/2000 | Passafaro et al. |
| 6,206,898 | B1 | 3/2001 | Honeycutt et al. |
| 6,258,061 | B1 | 7/2001 | Drasler et al. |
| 6,361,545 | B1 | 3/2002 | Macoviak et al. |
| 6,371,969 | B1 * | 4/2002 | Tsugita et al. ............ 606/200 |
| 6,443,966 | B1 | 9/2002 | Shiu |
| 6,451,036 | B1 | 9/2002 | Heitzmann et al. |
| 6,454,779 | B1 | 9/2002 | Taylor |
| 6,471,683 | B2 | 10/2002 | Drasler et al. |
| 6,511,492 | B1 | 1/2003 | Rosenbluth et al. |
| 6,544,209 | B1 | 4/2003 | Drasler et al. |
| 6,558,366 | B1 | 5/2003 | Drasler et al. |
| 6,629,953 | B1 | 10/2003 | Boyd |
| 6,635,070 | B2 * | 10/2003 | Leeflang et al. ............ 606/200 |
| 6,652,548 | B2 | 11/2003 | Evans et al. |
| 6,676,627 | B1 | 1/2004 | Bonnette et al. |
| 6,719,718 | B2 | 4/2004 | Bonnette et al. |
| 6,764,483 | B1 | 7/2004 | Bonnette et al. |
| 6,805,684 | B2 | 10/2004 | Bonnette et al. |
| 6,824,551 | B2 | 11/2004 | Trerotola |
| 6,926,726 | B2 | 8/2005 | Drasler et al. |
| 6,945,951 | B1 | 9/2005 | Bonnette et al. |
| 6,945,977 | B2 | 9/2005 | Demarais et al. |
| 6,984,239 | B1 | 1/2006 | Drasler et al. |
| 7,108,704 | B2 | 9/2006 | Trerotola |
| 2004/0098033 | A1 | 5/2004 | Leeflang |
| 2004/0153118 | A1 | 8/2004 | Clubb et al. |
| 2006/0064123 | A1 | 3/2006 | Bonnette et al. |
| 2008/0109088 | A1 | 5/2008 | Galdonik et al. |
| 2008/0234722 | A1 | 9/2008 | Bonnette et al. |
| 2010/0185210 | A1 | 7/2010 | Hauser |
| 2010/0268264 | A1 | 10/2010 | Bonnette et al. |

OTHER PUBLICATIONS

Supplementary European Search Report from corresponding application, dated May 16, 2012.

International Search Report and Written Opinion from related application No. PCT/US12/38499 dated Aug. 31, 2012.

* cited by examiner

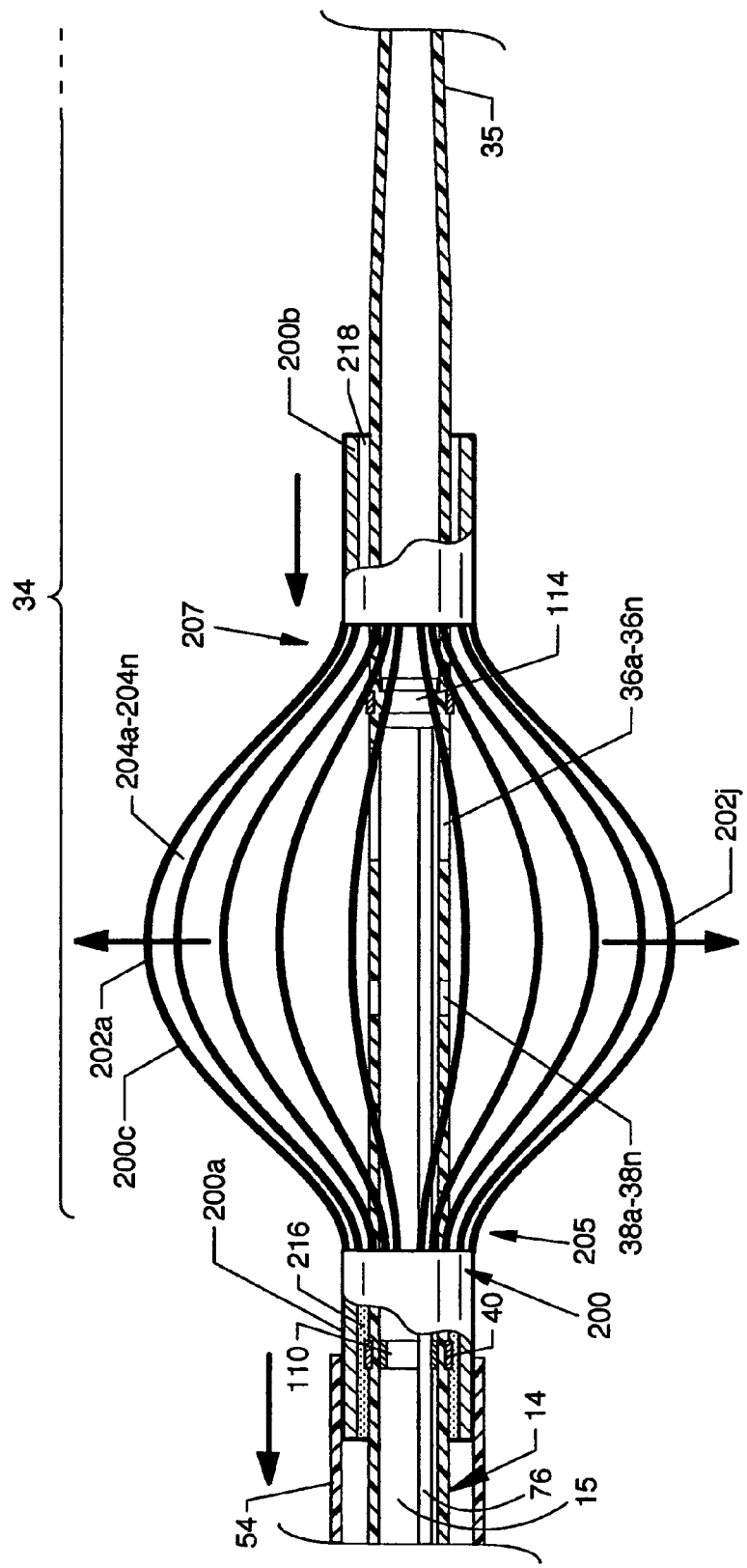

CROSS STREAM THROMBECTOMY CATHETER WITH FLEXIBLE AND EXPANDABLE CAGE

CROSS REFERENCES TO RELATED APPLICATIONS

None.

BACKGROUND OF THE INVENTION

1. Field of the Invention

The present invention is for a thrombectomy catheter, and more particularly, relates to a cross stream thrombectomy catheter with a flexible and expandable cage which is deployable and expandable about the distal region of the cross stream thrombectomy catheter for abrasive contact with and for abrasive removal of hardened thrombus or other foreign material in addition to and in cooperation with ablative cross stream flow. This device is used in the removal of tissues or highly organized, old thrombus in the most difficult of cases where simple water jet thrombectomy procedures may be ineffective.

2. Description of the Prior Art

Prior art thrombectomy catheters incorporating water jet technology encounter difficulty in dealing with old and difficult thrombus. Thrombus consistency can vary tremendously depending upon factors such as the age of the clot, conditions under which it was formed, the hematology of the patient and other factors. This is especially true in the case of deep vein thrombosis, where the thrombus can vary from fresh soft clot to older more organized clot. This more organized thrombus is the most difficult to remove. Furthermore, the large veins in the legs present the need to remove large volumes of clot that are not only larger in diameter but can extend for longer distances. In the case of lysins, the distances the chemical must diffuse is longer. This results in longer treatment times and hence more complications, such as hemorrhagic stroke. In the case of mechanical agitators, such as the Bacchus Trellis device, the device is limited in its operating diameter. If the device is designed to operate in a large diameter, the forces to operate the device would increase and the mechanical integrity of the agitator would need to increase (i.e., diameter of the wire) would grow larger, both of which make the device more difficult to deliver and operate. The use of the AngioJet®, a rheolytic cross stream thrombectomy catheter, includes an inherent ability to remove thrombus of larger diameter than the catheter's diameter. However, the disruptive strength of the device falls off with the radial distance from the catheter. Hence, at some radial distance the clot is stronger than the disruptive force generated by the AngioJet® cross stream flow patterns. In the case of organized thrombus, this radial distance from the catheter is smaller than for softer thrombus. The present invention adds another dimension to water jet thrombectomy by dealing with very difficult thrombus. Water jet thrombectomy procedures in general can be limited in ability, but adding mechanical disruption of difficult to remove thrombus to water jet ablation is actually taking thrombectomy procedures to another level. By combining mechanical agitation; i.e., abrasive intimate contact of thrombus by a flexible and expandable cage component, with a rheolytic thrombectomy catheter (AngioJet®), larger diameters of thrombus can be cleared than can be cleared by mechanical agitators or rheolytic cross stream thrombectomy catheters individually. This combination also extends to combining the use of the AngioJet® with lysins. By disrupting thrombus with flow, the lysins can be mixed better with the thrombus, and the lysins soften the clot such that AngioJet® is more effective. Furthermore, such a technique enables shorter treatment times compared to the use of either AngioJet® or lysins alone. Consequently, the combination of mechanical agitators with AngioJet® and even with lysins represents synergistic efficiencies in the removal of thrombus.

SUMMARY OF THE INVENTION

The general purpose of the present invention is to provide a cross stream thrombectomy catheter with a flexible and expandable cage formed, preferably, of nitinol, and to provide a method of use. This disclosure describes the invention of a cross stream thrombectomy catheter combined with flexible and expandable nitinol cages which are expandable and deployable at the distal region by action of a positionable assembly. At times, thrombus in vessels may be so old and so organized that water jet thrombectomy procedures become ineffective at removing this material. In terms of mechanical advantage, a solid material, such as metal, can apply a force that is magnitudes higher than a fluid. The use of a rigid member can apply much more force to a substance than a fluid can, as fluids tend to take the path of least resistance and may flow around debris rather than remove it. However, a rigid member, if designed correctly, will be more effective in "ploughing" through a material and disrupting the material and will be able to disrupt even the most difficult of materials found within blocked vessels. Therefore, flexible and expandable nitinol cages of suitable porous qualities and configurations have been combined with a water jet thrombectomy catheter to optimize ability to remove very difficult tissues within vessels. When combined therewith, the flexible and expandable cages are used in a fashion similarly used as a grater to aggressively break up the difficult to remove thrombus material, whereas the water jet thrombectomy catheter is used to wash and flush the blood vessel and remove both loosened soft and difficult to remove thrombus debris.

The first embodiment of the instant invention includes a catheter tube having distally located inflow and outflow orifices with a distally located flexible and expandable nitinol mesh cage located over and about the distal end of the catheter tube, and more specifically, over and about the inflow and outflow orifices. A manifold connects to the proximal end of the catheter tube, the manifold providing for connection to pressurizing and evacuation equipment known in the art. A positionable assembly having a sheath and a connected manual actuator is located coaxially about the catheter tube. The distal end of the sheath is connected to a free-floating proximal end of the flexible and expandable cage of nitinol mesh, and the proximal end of the sheath is connected to the manual actuator. The distal end of the flexible and expandable mesh cage is fixedly secured to the catheter tube at a fixed position at or near the distal end of the catheter tube. The manual actuator is slideably positioned along the catheter tube to correspondingly urge movement of the sheath to displace the proximal end of the flexible and expandable mesh cage with respect to the distal end of the flexible and expandable mesh cage to deploy and expand the flexible and expandable mesh cage or to collapse and retract the flexible and expandable mesh cage. In use, the catheter tube and portion of the positionable assembly are advanced to and through a thrombus site, wherein the flexible and expandable mesh cage is expanded and deployed and actuated in a to and fro action, a rotary action, or a combination thereof, where such actions are incorporated by intimate contact to abrade, grate, scrape, or otherwise loosen and dislodge difficult to remove thrombus. Loosened thrombus can be acted upon by cross stream jets for entrainment for maceration and/or for evacuation through the catheter tube. When the flexible and expandable cage is collapsed and retracted, the catheter tube can be maneuvered from the former thrombus site and from the vasculature. A first alternative embodiment includes the majority of structure of the device just described, but substitutes a mechanism in which a threaded tube rotatingly engages an internally threaded sleeve to rotatably and incrementally operate the sheath and flexible and expandable mesh cage to deploy and expand the flexible and expandable mesh cage to a known and indicated specific size parameter and to maintain such specific size at a desired setting as required.

According to one or more embodiments of the present invention, there is provided a cross stream thrombectomy catheter with a flexible and expandable mesh cage including a manifold, an introducer, a catheter tube connected to the manifold, inflow and outflow orifices at the distal end of the catheter tube, a high pressure tube with a fluid jet emanator, a flexible and expandable mesh cage preferably of nitinol material having a distal and stationary end attached to the distal region of the catheter tube, a positionable assembly including a manual actuator and attached sheath which is positionable, each aligned over and about the greater portion of the catheter tube where the distal end of the sheath attaches to the proximal and positionable end of the flexible and expandable mesh cage and the proximal end of the sheath attaches to a positionable hand actuator where the positionable assembly is coaxial to and operated along and about a central region of the catheter tube. Alternatively and in other embodiments, a flexible and expandable cage having straight or spiral filament construction, preferably of preshaped and preformed nitinol material, includes a proximal end fixed to the catheter tube rather than to the sheath and a distal end freely and slideably aligned over and about the catheter tube. In these embodiments, the distal portion of the sheath slides over the flexible and expandable cage having straight or spiral filament construction and compresses the preshaped and preformed nitinol material of the flexible and expandable cage having straight or spiral filament construction for insertion into the vasculature to await later urging of the sheath proximally to reveal and allow expansion of the flexible and expandable cage having straight or spiral filament construction. The flexible and expandable cages having straight or spiral filament construction can be advanced to and through a thrombus site, wherein the flexible and expandable cages having straight or spiral filament construction are expanded and deployed and actuated in a to and fro action, a rotary action, or a combination thereof in a manner as previously described for the first embodiment, where such actions are incorporated by intimate contact to abrade, grate, scrape, or otherwise loosen and dislodge difficult to remove thrombus. An additional benefit of the use of the flexible and expandable cages having straight or spiral filament construction is that some loosened and dislodged thrombus particulate can frictionally engage the converging filaments at each end of the cage or be captured by surrounding collapsed cage structure and be removed from the thrombus site when the catheter and cage are withdrawn from the thrombus site.

Such alternative embodiments include other configurations of flexible and expandable cages, preferably of nitinol material, wherein a cut tube of nitinol is fashioned having opposed uncut distal and proximal tube ends and either straight filament or spiral filament central sections between the opposed uncut distal and proximal tube ends.

One significant aspect and feature of the present invention is a cross stream thrombectomy catheter that is combined with a flexible and expandable mesh cage or a straight or spiral filament flexible and expandable cage for the purpose of removing highly organized, old thrombus.

Another significant aspect and feature of the present invention is a cross stream thrombectomy catheter combined with a flexible and expandable mesh cage or a straight or spiral filament flexible and expandable cage, each such cage serving as a mechanical agitator and/or cutter device.

Still another significant aspect and feature of the present invention is a cross stream thrombectomy catheter combined with a flexible and expandable mesh cage that is deployed by the action of a sheath which is placed over the catheter tube and moved along the catheter tube by manual action.

A further significant aspect and feature of the present invention is a cross stream thrombectomy catheter which can incorporate rapid exchange technology in combination with a flexible and expandable mesh cage or a straight or spiral filament flexible and expandable cage.

Yet another significant aspect and feature of the present invention is a cross stream thrombectomy catheter combined with a flexible and expandable cage that is made of a nitinol mesh or other configuration of nitinol and that has its distal end fixed to a catheter tube and its proximal end attached to a sheath so as to move freely with the sheath and along the catheter tube between deployed and collapsed positions.

A further significant aspect and feature of the present invention is a cross stream thrombectomy catheter combined with a flexible and expandable preset memory shape nitinol cage that is caused to deploy via the action of a sheath which exposes and reveals the preset memory shape nitinol cage. The preset memory shape nitinol cage is attached only at its proximal end to the catheter tube, the distal end being free to slide along the catheter tube.

Still another significant aspect and feature of the present invention is a cross stream thrombectomy catheter combined with a flexible and expandable cage that is of a straight nitinol filament design, or of a spiral nitinol filament design, or of some other nitinol configuration or design and that has its proximal end fixed to a catheter tube and its distal end free to move freely along the catheter tube by action of a sheath which revealingly deploys or collapses and captures the flexible and expandable straight nitinol filament design cage, or spiral nitinol filament design cage, or other nitinol configuration or design cage.

Another significant aspect and feature of the present invention is the use of flexible and expandable cages of various designs which, with respect to thrombus, can be actuated in to and fro motion, rotary motion, or motion combinations.

Yet another significant aspect and feature of the present invention is the use of flexible and expandable cages of nitinol mesh or straight or spiral filaments of nitinol which can be heat set to maintain a predetermined memory shape.

A still further significant aspect and feature of the present invention is a cross stream thrombectomy catheter combined with a flexible and expandable mesh cage, a straight filament flexible and expandable cage, or a spiral filament flexible and expandable cage, which can be over the outflow and inflow orifices, distal to the outflow and inflow orifices, or somewhere proximal to the outflow and inflow orifices.

A further significant aspect and feature of the present invention is a cross stream thrombectomy catheter which can use saddle jet emanator or other jet emanator technology combined with a flexible and expandable mesh cage, a straight filament flexible and expandable cage, or a spiral filament flexible and expandable cage.

A further significant aspect and feature of the present invention is a cross stream thrombectomy catheter combined with a flexible and expandable mesh cage or with a straight or spiral filament flexible and expandable cage that is deployed from a location about the catheter tube.

Another significant aspect and feature of the present invention is the capture of loosened thrombus particles by converging straight or spiral filaments of nitinol in flexible and expandable cages and/or by the collapsed cage structure.

Still another significant aspect and feature of the present invention is a cross stream thrombectomy catheter combined with a flexible and expandable mesh cage or with a straight or spiral filament flexible and expandable cage that is deployed by the action of a sheath which is located over and about the catheter tube and moved along the catheter tube by a screw-type arrangement having size indication to gain precise expansion control instead of being moved in a less precise manual fashion.

Still another significant aspect and feature of the present invention is a cross stream thrombectomy catheter with a flexible and expandable mesh cage, or a straight or spiral filament flexible and expandable cage, which can be utilized solely as a cross stream thrombectomy catheter without exercising the abrading functions of the flexible and expandable mesh cage, or the straight or spiral filament flexible and expandable cage.

A further significant aspect and feature of the present invention is a cross stream thrombectomy catheter that uses guidewire position directional flow technology, such as is disclosed in copending patent application Ser. No. 11/009,720 entitled "Enhanced Cross Stream Mechanical Thrombectomy Catheter with Backloading Manifold" filed on Dec. 10, 2004, combined with a flexible and expandable cage.

Having thus briefly described embodiments of the present invention and having mentioned some significant aspects and features of the present invention, it is the principal object of the present invention to provide a cross stream thrombectomy catheter with a flexible and expandable cage.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
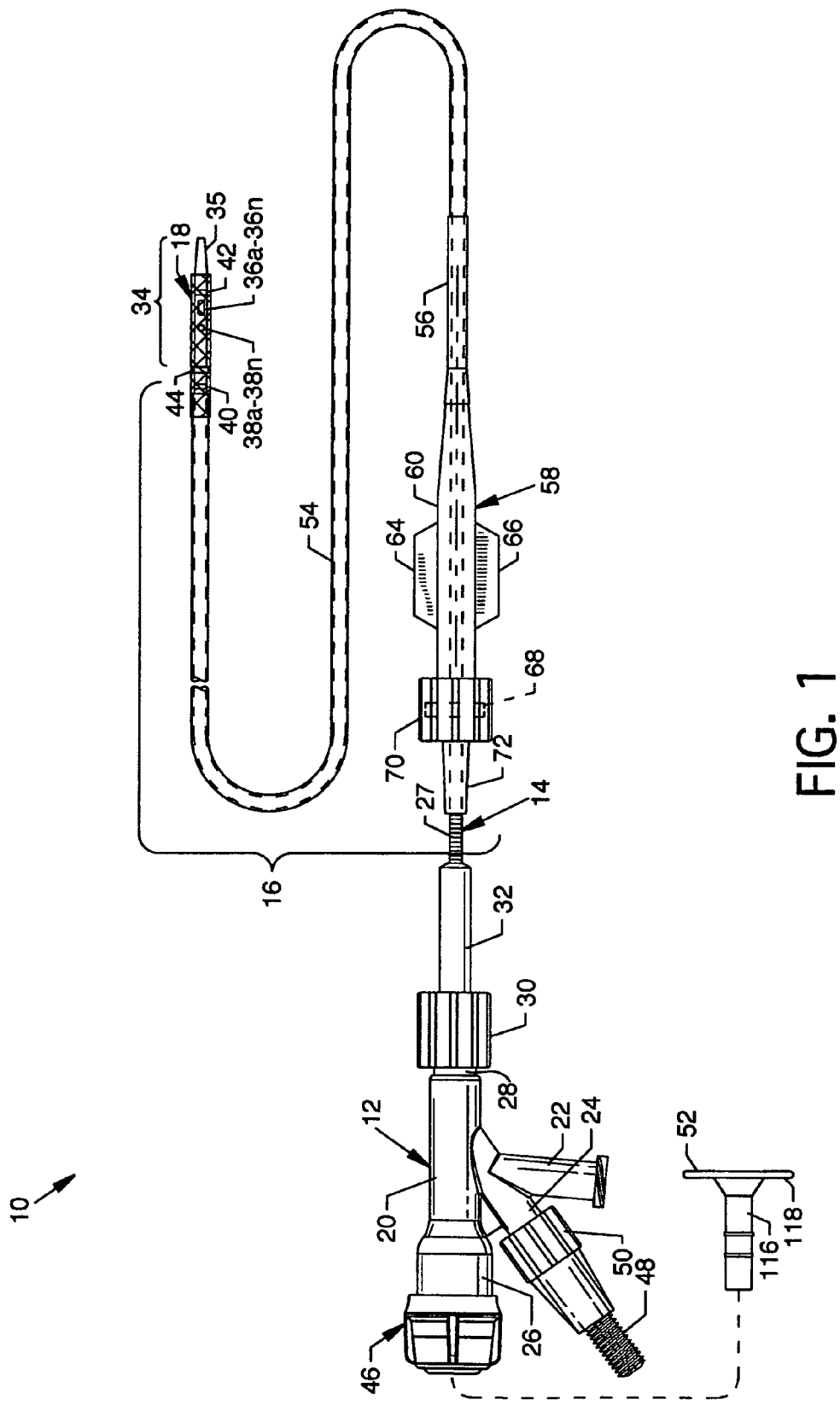
FIG. 1 is a plan view of the visible components of a cross stream thrombectomy catheter with a flexible and expandable cage constituting one embodiment of the present invention.
Figure 2:
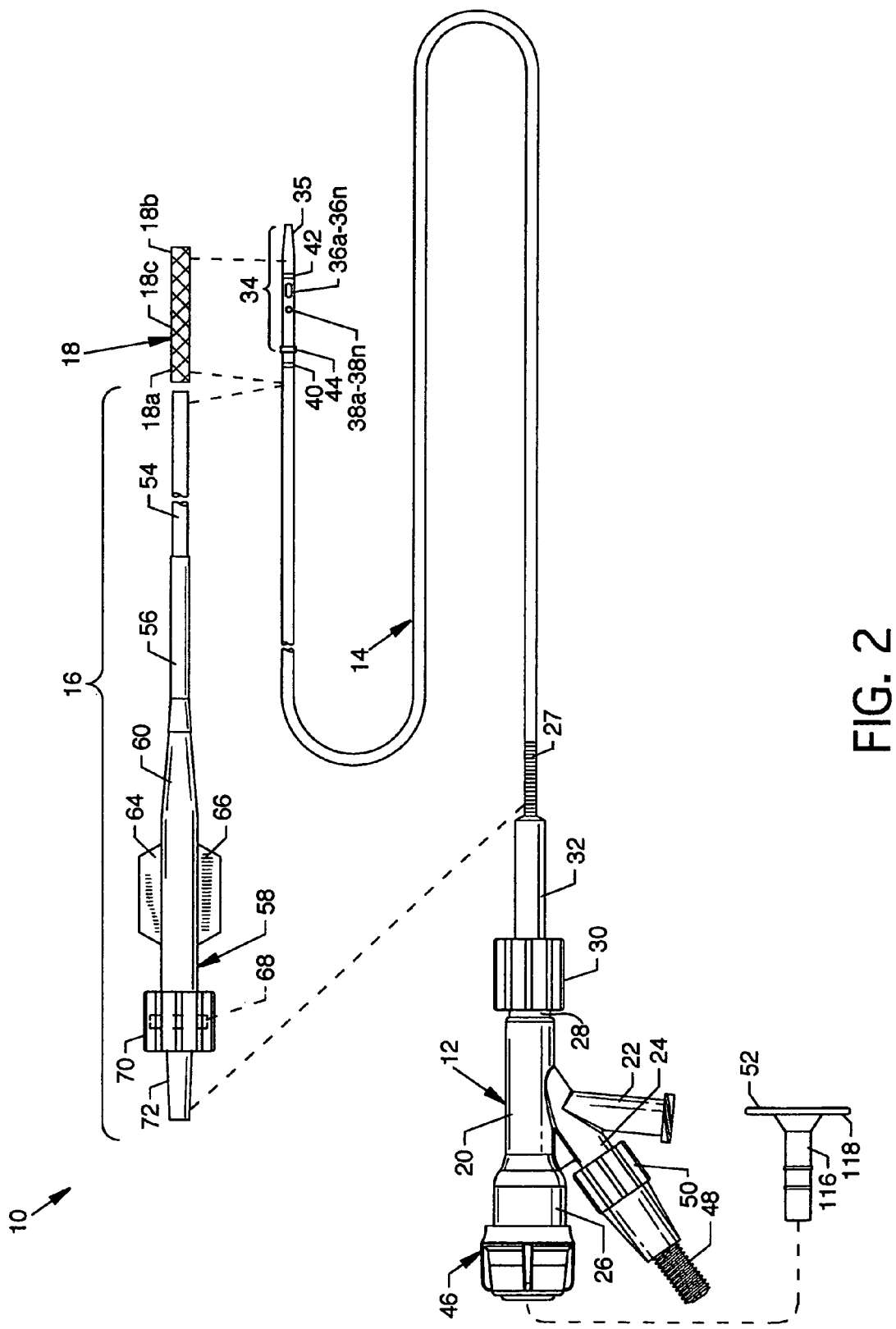
FIG. 2 shows the elements of FIG. 1 where major components and assemblies have been separated to facilitate description.

FIG. 1 is a plan view of the visible components of a cross stream thrombectomy catheter with flexible and expandable cage 10 constituting an embodiment of the present invention, and FIG. 2 shows the elements of FIG. 1 where major components and assemblies have been separated to facilitate description. Such major components and assemblies include a one-piece manifold 12 having multiple structures extending therefrom or attached thereto, a catheter tube 14, a positionable assembly 16, and a tubular-shaped flexible and expandable mesh cage 18 including a proximal end 18a which is connected to the distal end of a sheath 54 at the distal end of the positionable assembly 16, and including a distal end 18b which is attached to the distal region of the catheter tube 14. A central section 18c of the flexible and expandable mesh cage 18 is located between the proximal end 18a and the distal end 18b of the flexible and expandable mesh cage 18.

The visible portion of the one-piece manifold 12 includes a central tubular body 20, a high pressure connection branch 24 extending angularly from the central tubular body 20, an exhaust branch 22 extending angularly from the high pressure connection branch 24, a cavity body 26 extending proximally from the central tubular body 20, and a threaded connection port 28 partially shown extending distally from the central tubular body 20. The proximal region of the catheter tube 14 includes incremental markings 27 and secures to the manifold 12 by the use of a connector 30 accommodated by the threaded connection port 28. The proximal end of the catheter tube 14 extends through and seals against the interior of a strain relief 32 and through the connector 30 to communicate with the manifold 12. The catheter tube 14, including a lumen 15 (FIG. 3), extends distally to a tip 34 having a tapered portion 35, the catheter tube 14 and tip 34 including the tapered portion 35 being flexible in design. The tip 34 of the catheter tube 14 includes a plurality of inflow orifices 36a-36n and a plurality of outflow orifices 38a-38n, and also includes radiopaque marker bands 40 and 42, the function of which are disclosed and described in detail in previous patent applications and patents owned by the assignee. A stop 44, which can be annular and which is best illustrated in FIG. 5c, is also secured around and about the tip 34 at the distal portion of the catheter tube 14. Also shown is a hemostatic nut 46 aligned to and snappingly engaged with the proximal region of the cavity body 26 and a threaded high pressure connection port 48 secured to the high pressure connection branch 24 by a Luer connector 50. An introducer 52 is also shown.

FIG. 1 shows the positionable assembly 16 and the flexible and expandable mesh cage 18 engaged over and about various portions of the catheter tube 14, and FIG. 2 shows the positionable assembly 16 and flexible and expandable mesh cage 18 removed from, distanced from, and shown separately from the catheter tube 14 for the purpose of clarity. The flexible sheath 54 is appropriately sized to be slidingly engaged over the catheter tube 14. The sheath 54 extends along the length of the catheter tube 14 where the distal end of the sheath 54 aligns to a variable location at or near the tip 34 which is short of the radiopaque marker band 40, preferably as shown in FIG. 5c. The proximal end of the sheath 54 aligns within the distal end of a strain relief tube 56 and secures suitably therein, as shown in FIG. 5b. The flared proximal end of the strain relief tube 56 aligns with and about the tapered distal end of a manual actuator 58 shown in detail in FIG. 5b such manual actuator 58 having a tubular body 60, a passage 62, handles 64 and 66, and a proximally located threaded end 68. A connector 70 having a tubular extension 72 extending continuously therefrom engages the threaded end 68 of the manual actuator 58.

Figure 3:
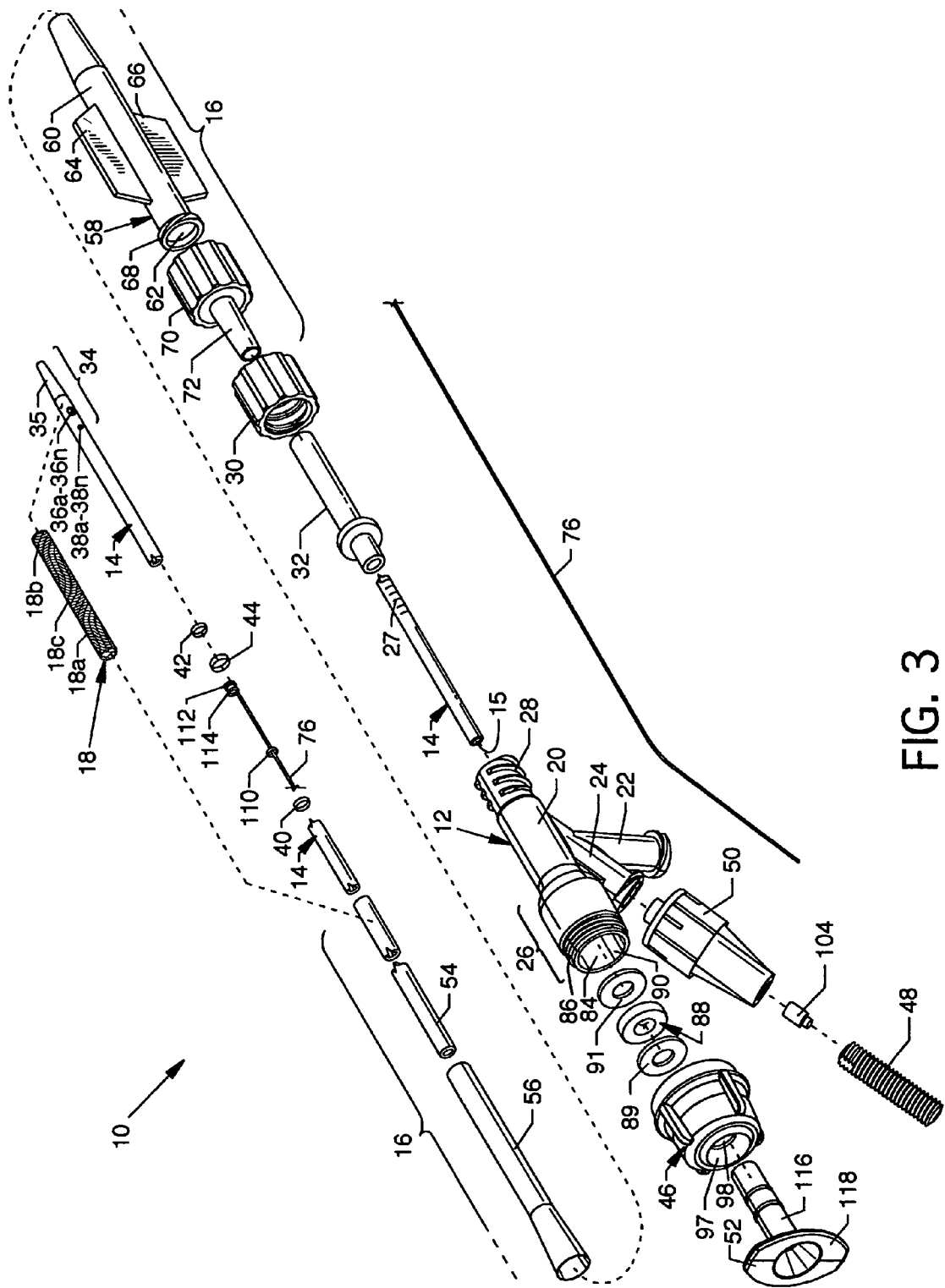
FIG. 3 is an exploded isometric view of the cross stream thrombectomy catheter with flexible and expandable cage.
Figure 4:
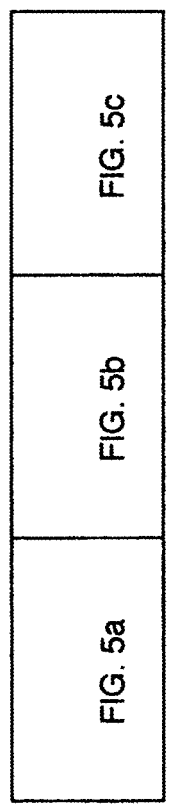
FIG. 4 illustrates the alignment of FIGS. 5a, 5b and 5c.
Figure 5A:
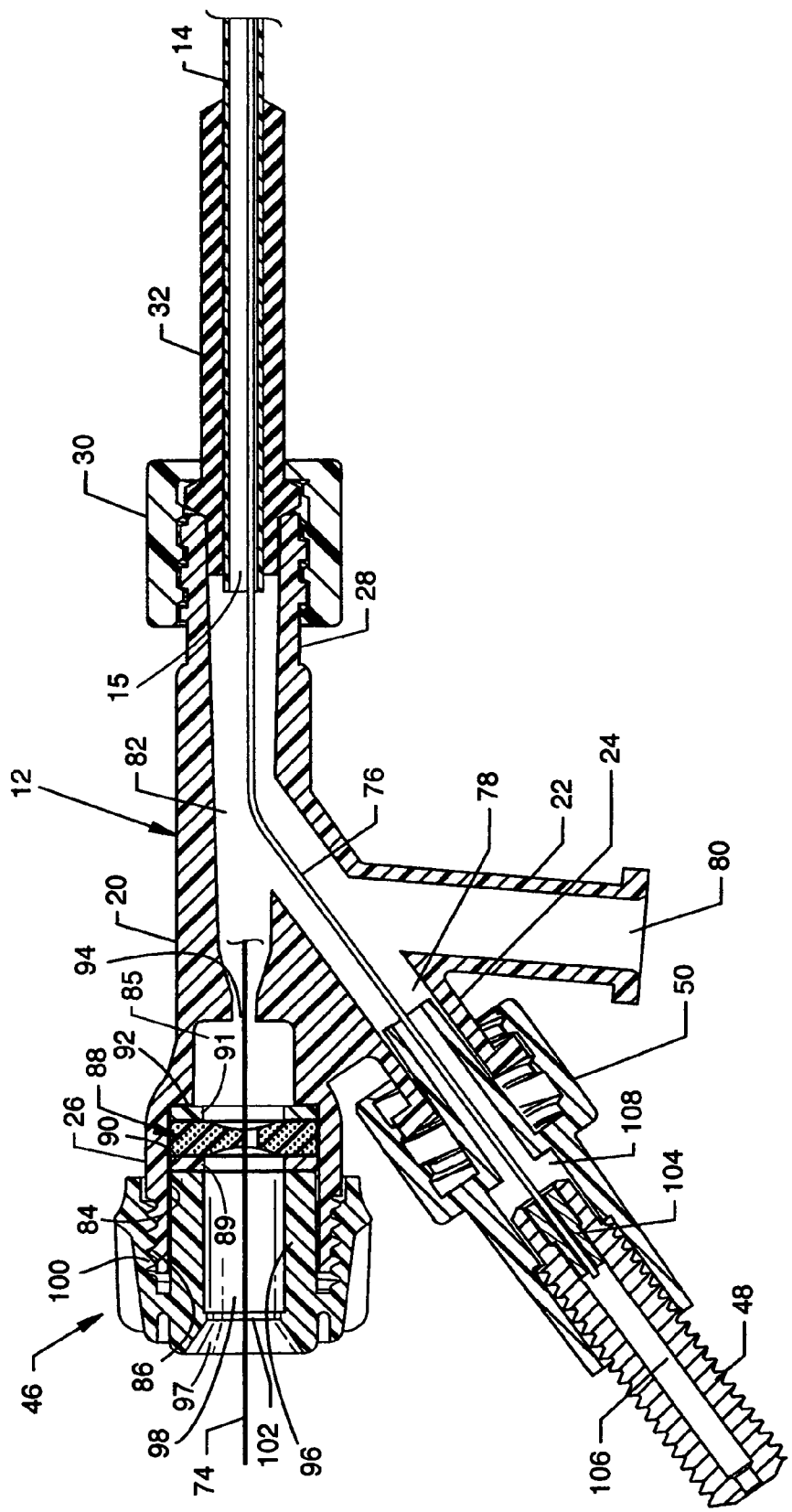
FIGS. 5a, 5b and 5c together illustrate a side view in partial cross section of the components of the aforementioned cross stream thrombectomy catheter with flexible and expandable cage showing only part of the full length of the catheter tube and, in FIG. 5a, depicting a portion of a guidewire.
Figure 5B:
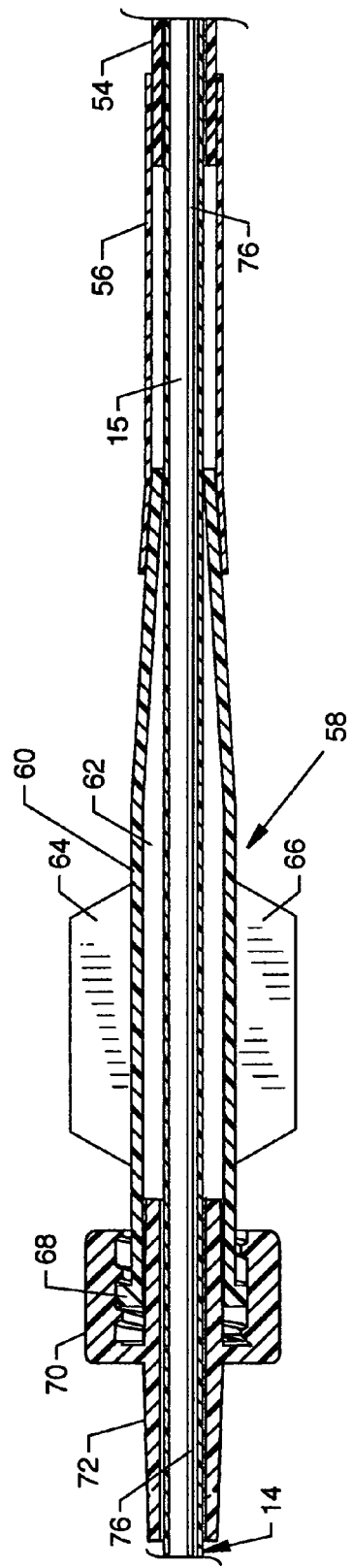
Figure 5C:
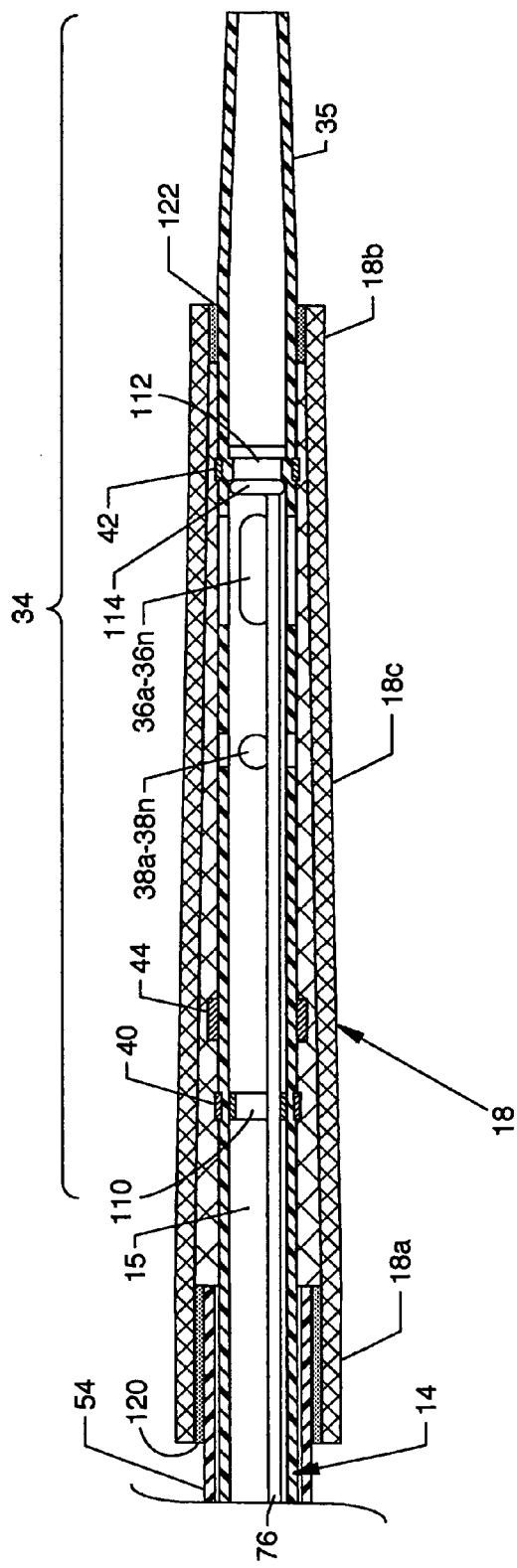

FIG. 3 is an exploded isometric view of the cross stream thrombectomy catheter with flexible and expandable cage 10, and FIGS. 5a, 5b and 5c, aligned as shown in FIG. 4, together illustrate a side view in partial cross section of the components of the cross stream thrombectomy catheter with flexible and expandable cage 10 showing only part of the full length of the catheter tube 14 and depicting a portion of a guidewire 74 (FIG. 5a) such as is incorporated in the use thereof. FIG. 5c is illustrated in a scale slightly larger than that of FIGS. 5a and 5b for the purpose of clarity. The catheter tube 14, which also serves and functions as an exhaust tube, and a high pressure tube 76 are foreshortened and shown as partial lengths for the purpose of clarity.

With reference to FIG. 3 and FIGS. 5a, 5b and 5c together, the instant embodiment is further described. The manifold 12 includes connected and communicating passageways and cavities including a high pressure connection branch passageway 78 within the high pressure connection branch 24, an exhaust branch passageway 80 within the exhaust branch 22, and a tapered central passageway 82 extending from and through the threaded connection port 28 and through the central tubular body 20, through an orifice 94, through a cavity extension 85, to and communicating with a cavity 84, which preferably is cylindrical, located central to the cavity body 26. Threads 86 are located about the exterior of the cavity body 26 at the proximal region of the manifold 12.

Beneficial to the instant embodiment is the use of a self-sealing hemostatic valve 88 the shape of and the functions of which are described later in detail. The self-sealing hemostatic valve 88 is aligned in and housed in the cavity 84 at the proximal region of the manifold 12 along with flexible washers 89 and 91 which align to opposing sides of the self-sealing hemostatic valve 88. The cavity 84 is tubular including a cavity wall 90 and a planar surface 92 which is annular and circular and which intersects the cavity wall 90. The orifice 94 is common to the cavity extension 85 and the tapered central passageway 82. The hemostatic nut 46 includes a centrally located cylindrical boss 96, a beveled entryway 97 leading to a passageway 98 extending through and in part defining the cylindrical boss 96, and internal threads 100. The proximal end of the manifold 12 utilizes the threads 86 for attachment of the hemostatic nut 46 to the manifold 12 where the internal threads 100 of the hemostatic nut 46 rotatingly engage the threads 86 of the manifold 12 to cause the cylindrical boss 96 to bear directly against the flexible washer 89 to cause the self-sealing hemostatic valve 88 to expandingly seal against the guidewire 74 where such sealing is effective during static or actuated states of the manual actuator 58. The self-sealing hemostatic valve 88 and flexible washers 89 and 91 are captured in the distal region of the cavity 84 by engagement of the hemostatic nut 46 to the cavity body 20 of the manifold 12. Use of the flexible washers 89 and 91 is incorporated to minimize distortion of the hemostatic seal 88 when the cylindrical boss 96 is tightened to compress the hemostatic valve 88. Also included in the hemostatic nut 46 is an annular lip 102 which can be utilized for snap engagement of an introducer 52 or other particular styles or types of introducers, as required.

Also shown is a ferrule 104 which aligns within a passageway 106 of the threaded high pressure connection port 48, the combination of which aligns partially within the interior passageway 108 of the Luer connector 50. One end of the high pressure tube 76 is utilized for delivery of high pressure ablation liquids and suitably secures in a center passage of the ferrule 104 to communicate with the passageway 106 of the threaded high pressure connection port 48. The high pressure tube 76 also extends through the high pressure connection branch passageway 78, through part of the tapered central passageway 82, through coaxially aligned components including lumen 15 in the catheter tube 14, the connector 30 and the strain relief 32, thence through the balance of the length of the lumen 15 in the catheter tube 14, through support ring 110 and radiopaque marker band 40, through the stop 44, and to the grooved support ring 112 at the tip 34 where termination is provided in the form of a fluid jet emanator 114 described in other applications and patents owned by the assignee. The high pressure tube 76 can also be attached to the support ring 110, such as by welding or other suitable means, and can function as support for the catheter tube 14 in the region beneath the radiopaque marker 40. Support of the catheter tube 14 in the region beneath the radiopaque marker 42 can be provided by the grooved support ring 112 which is connected to and which extends from the fluid jet emanator 114. The introducer 52 having a centrally located hollow shaft 116 and an actuating handle 118 is also shown.

In FIGS. 2 and 3, the flexible and expandable mesh cage 18, preferably of nitinol, is shown separated from the general structure of the invention involving the distal end of the positionable assembly 16 at the distal end of the sheath 54 and involving the distal portion of the catheter tube 14 just distal of the radiopaque marker band 42. Shown particularly in FIG. 5c is the attachment of the flexible and expandable mesh cage 18. Adhesive 120 is utilized to attach the proximal end 18a of the flexible and expandable mesh cage 18 to the distal end of the sheath 54, and adhesive 122 is utilized to attach the distal end 18b of the flexible and expandable mesh cage 18 to the distal end of the catheter tube 14 adjacent to a tapered portion 35. Also shown is the radiopaque marker 40 secured over and about the catheter tube 14 and the underlying support ring 110 as well as the radiopaque marker 42 secured over and about the catheter tube 14 and underlying grooved support ring 112. The annular stop 44 is also shown appropriately secured over and about the catheter tube 14 to limit distal movement of the sheath 54 along and about the catheter tube 14. The fluid jet emanator 114 is shown secured by association with the grooved support ring 112 within the catheter tube 14 distal to the inflow orifices 36a-36n.

Mode of Operation

Figure 6:
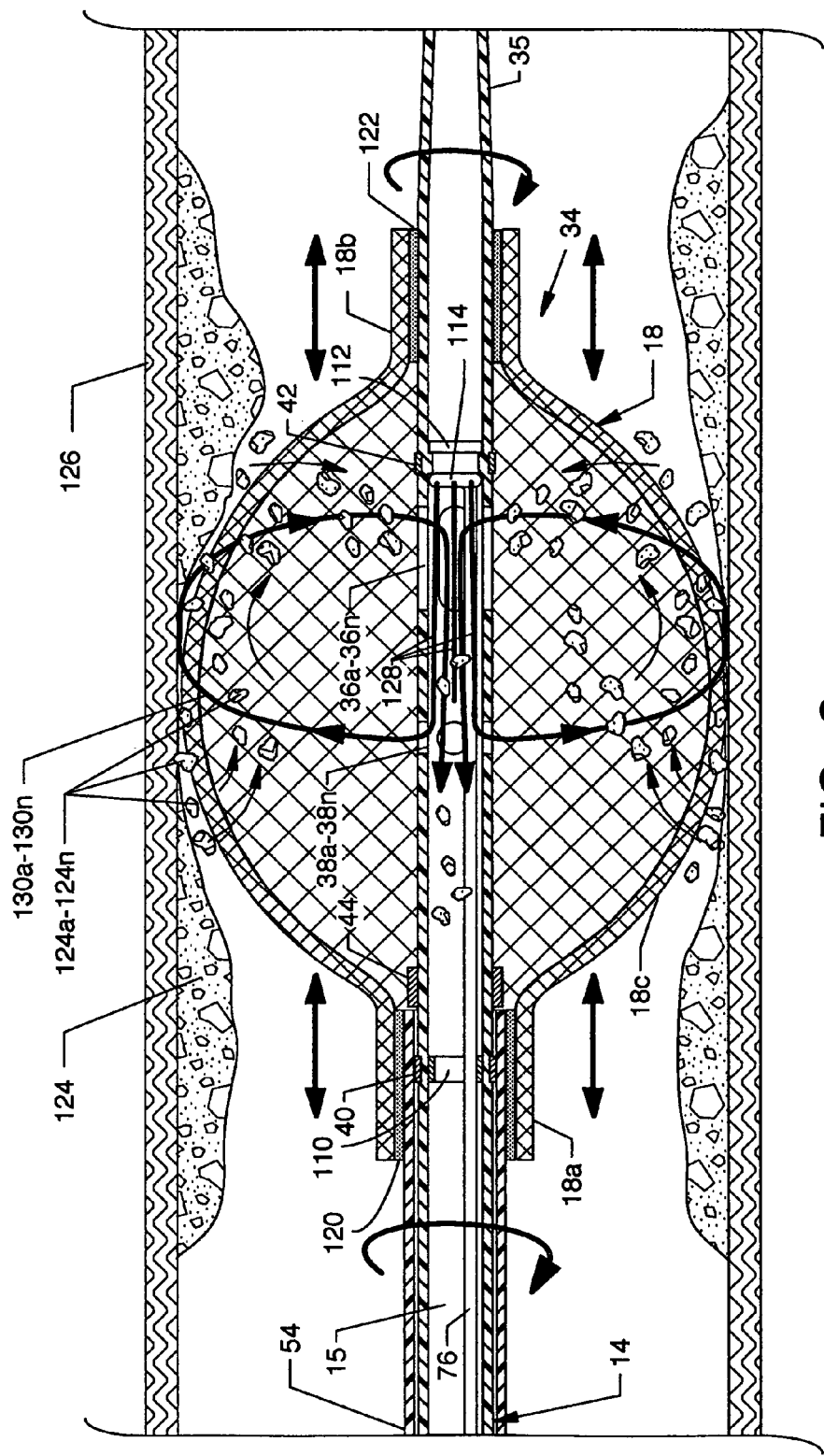
FIG. 6 is a view in cross section showing the tip and the flexible and expandable mesh cage and other important and related components of the aforementioned cross stream thrombectomy catheter with flexible and expandable cage engaged in the dislodging and extraction of difficult to remove thrombus or other types of objectionable material adhering, clinging or otherwise affixed to the interior wall of a blood vessel.

FIG. 6 is a view in cross section showing the tip 34 and the flexible and expandable mesh cage 18 and other important and related components of the cross stream thrombectomy catheter with flexible and expandable cage 10 engaged in the dislodging and extraction of difficult to remove thrombus 124 or other types of objectionable material adhering, clinging or otherwise affixed to the interior wall of a blood vessel 126. A high pressure source as commonly utilized in the art is utilized to supply high pressure delivery of saline or other suitable medium to the threaded high pressure connection port 48 for delivery by the high pressure tube 76 to the fluid jet emanator 114; and a vacuum source as known in the art may be utilized to aid in evacuation of the catheter tube 14 through connection to the exhaust branch 22. With reference to FIG. 6 and implied reference to previously described figures, the mode of operation is further described.

In practice, the cross stream thrombectomy catheter with flexible and expandable cage 10 is engaged over and about the previously shown guidewire 74, which would have been previously inserted into the vasculature of a patient until the tip 34 and the flexible and expandable mesh cage 18 and other important and closely located related components negotiate passage through but remain within the general buildup area of thrombus 124. Such loading and engagement occurs where the proximal end of the guidewire 74 enters the tip 34 and lumen 15 of the catheter tube 14 and where the proximal guidewire tip is negotiated by the fluid jet emanator 114, the catheter tube 14, the tapered central passageway 82, and the orifice 94 which centers the guidewire 74 to the self-sealing hemostatic valve 88 and passage therethrough for sealing about the guidewire 74. Loading continues through the passageway 98 and beveled entryway 97 of the hemostatic nut 46. The guidewire 74 may or may not be removed depending upon future utilization requirements and is not shown in FIG. 6.

Upon suitable positioning within the vasculature, the cross stream thrombectomy catheter with flexible and expandable cage 10 is then utilized to engage and dislodge, loosen or otherwise displace difficult to remove thrombus 124 or other types of objectionable material adhering, clinging or otherwise affixed to the interior wall of a blood vessel 126 and break it into particulate suitable for removal through the flexible and expandable mesh cage 18 and through the lumen 15 of the catheter tube 14. To operate the device, the operator manually grasps both the manifold 12 and the manual actuator 58 and positions one or the other or both components to cause the positionable assembly 16 to be slidingly positioned in a distal direction with respect to the manifold 12 and the attached catheter tube 14. During such positioning, the translatory distal end of sheath 54 upon which the proximal end 18a of the flexible and expandable mesh cage 18 is secured is urged closer to the distal end 18b of the flexible and expandable mesh cage 18 which is secured in a fixed position about the tip 34. Such action causes forced outward deployment and expansion of the flexible and expandable mesh cage 18 where the central section 18c thereof expands radially to a rounded or bulbous conforming shape, whereby suitable intimate contact and engagement against the thrombus 124 occurs whether the thrombus is soft or is difficult to remove. The incremental markings 27 on the catheter tube 14 with reference to the proximal end of the tubular extension 72 of the connector 70 can be helpful to the operator in determining the degree or amount of expansion of the flexible and expandable mesh cage 18 before or during actual use of the cross stream thrombectomy catheter with flexible and expandable cage 10. Fluoroscopy, X-rays or other such suitable techniques also can be employed to view the positioning, expansion, progress and other desired aspects involving use of the cross stream thrombectomy catheter with flexible and expandable cage 10.

Once the flexible and expandable mesh cage 18 is properly positioned for use and expanded, as just described, the entire cross stream thrombectomy catheter with flexible and expandable cage 10 is actuated to incorporate intimate contact to abrade, grate, scrape or otherwise loosen and dislodge and remove thrombus 124, especially difficult to remove hardened thrombus, from the interior wall of the blood vessel 126, preferably with the simultaneous use of high pressure saline or other medium as emanated as fluid jet streams 128 from the fluid jet emanator 114 and by the introduction of suction in the lumen 15 of the catheter tube 14. Whilst maintaining the relative position of the manifold 12 and attached catheter tube 14 to the positionable assembly 16, the operator can reciprocatingly actuate the cross stream thrombectomy catheter with flexible and expandable cage 10 in a to and fro motion along the longitudinal axis of the catheter tube 14 and the flexible and expandable mesh cage 18 to cause the expanded and deployed flexible and expandable mesh cage 18 to frictionally abrade, grate, scrape or otherwise loosen and dislodge difficult to remove thrombus 124. The constitution of the flexible and expandable mesh cage 18 is a woven mesh having surfaces being suitable for loosening action including abrasion, grating and scraping when forcibly and movingly contacting the thrombus 124, as well as being suitable for the passage of thrombus particulate therethrough. Additional loosening action is also effective around and about the longitudinal axis where rotational actuation of the deployed flexible and expandable mesh cage 18 about the longitudinal axis of the catheter tube 14 and the flexible and expandable mesh cage 18 occurs. Combining the to and fro motion along the longitudinal axis of the flexible and expandable mesh cage 18 and the catheter tube 14 with the rotational actuation of the flexible and expandable mesh cage 18 about the longitudinal axis of the catheter tube 14 and the flexible and expandable mesh cage 18 results in multiple direction applied forcible loosening action to produce enhanced loosening.

Loosened thrombus particulates 124a-124n are produced by the loosening action including abrasion, grating and scraping incurred when forcibly and movingly contacting the thrombus 124, as just described, where such particulates 124a-124n are removed by interaction with cross stream jets 130a-130n. Fluid jet streams 128 projected rearwardly from the fluid jet emanator 114 along the catheter tube 14 exit the outflow orifices 38a-38n as a plurality of cross stream jets shown generally at 130a-130n and re-enter the relatively low pressure inflow orifices 36a-36n. Upon re-entry, a portion of the cross stream jets 130a-130n along with rearwardly directed flow of fluid jet streams 128 aided by suction applied at the exhaust branch 22 at the proximal end of the catheter tube 14 are exhausted through the exhaust branch 22 of the manifold 12. Accordingly, any thrombus particulates 124a-124n entrained therein are also exhausted through catheter tube 14 and the exhaust branch 22. As the flexible and expandable mesh cage 18 and the catheter tube 14 are actuated in one or more fashions, as previously described, for loosening of the thrombus 124, loosened thrombus particulates 124a-124n which first are located outside of the flexible and expandable mesh cage 18 are drawn through the open walls of the flexible and expandable mesh cage 18 and entrained by and into the flow of the cross stream jets 130a-130n. The cross stream jets 130a-130n are utilized in several other ways. Cross stream jets 130a-130n are used to pass through the central section 18c of the flexible and expandable mesh cage 18 to break loose and entrain any softer deposits of thrombus 124 which may still be attached to the interior wall of the blood vessel 126. The cross stream jets 130a-130n are further utilized for impinging ablation, maceration and breakdown of the thrombus particulates 124a-124n entrained therein and within the inner confines of the flexible and expandable mesh cage 18. The cross stream jets 130a-130n also deliver thrombus particulates 124a-124n through the inflow orifices 36a-36n for additional impingement and maceration by the fluid jet streams 128. In the above procedures, the introduction of lysins through the structure of the invention can be incorporated to further assist in the breaking down and softening of the soft or hard thrombus material.

Figure 7:
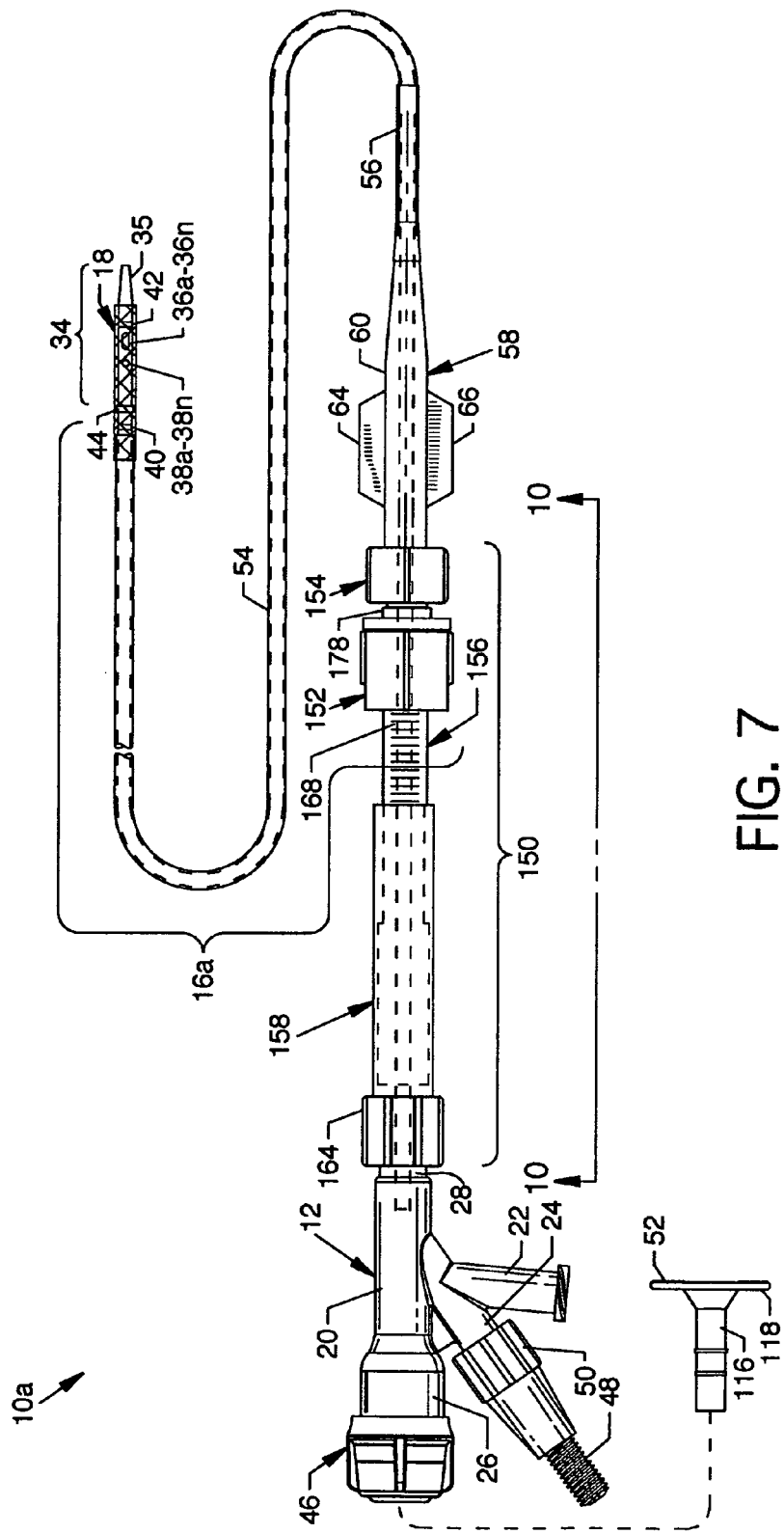
FIG. 7, a first alternative embodiment, is a plan view of the visible components of a cross stream thrombectomy catheter with flexible and expandable cage.
Figure 8:
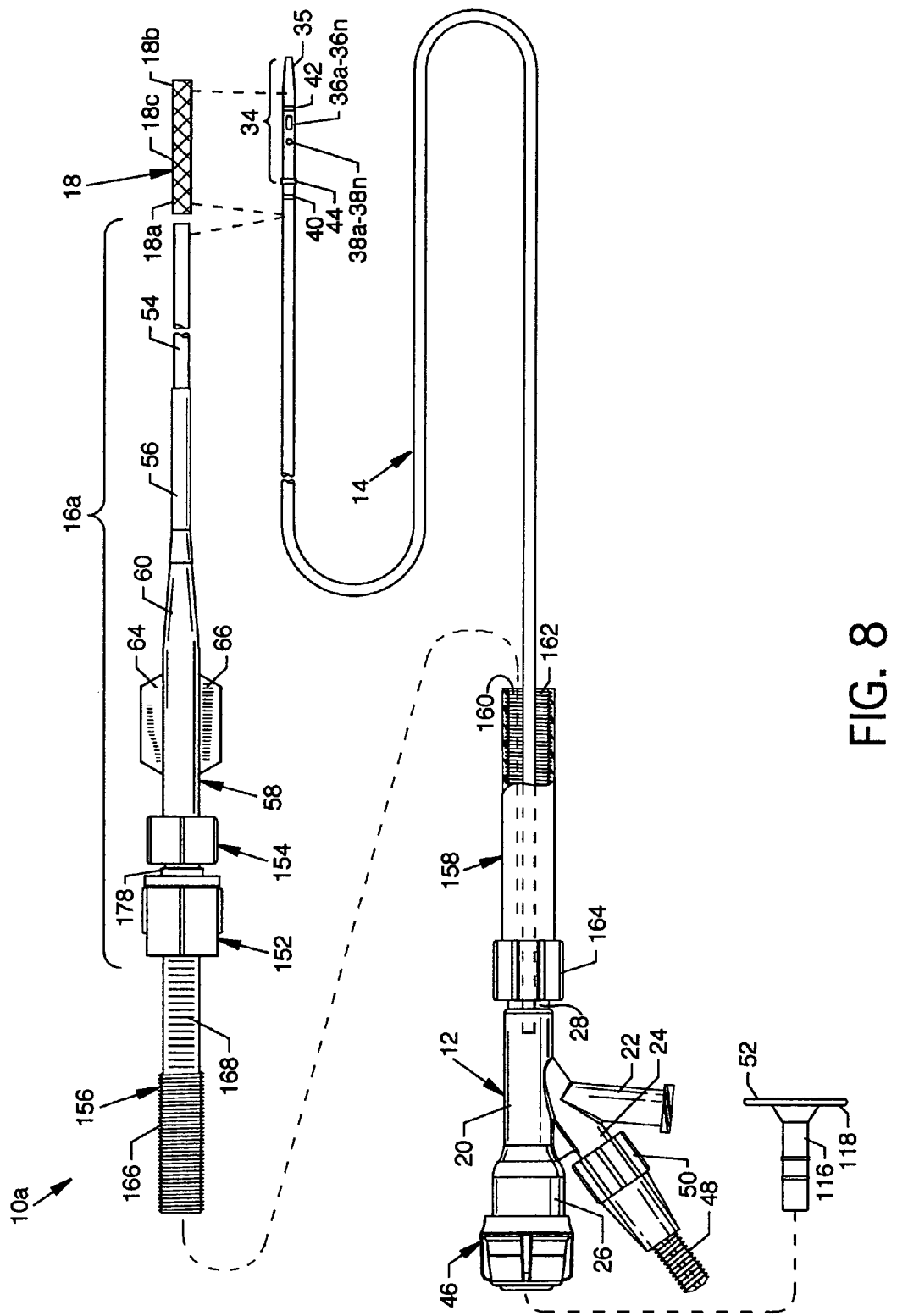
FIG. 8 shows the elements of FIG. 7 in a partially cutaway view where major components and assemblies have been separated to facilitate description.

FIG. 7, a first alternative embodiment, is a plan view of the visible components of a cross stream thrombectomy catheter with a flexible and expandable cage boa, and FIG. 8 shows the elements of FIG. 7 where major components and assemblies have been separated to facilitate description. The first alternative embodiment includes a rotary actuation system 150 for precise control of the opening, sizing, and incremental control of the flexible and expandable mesh cage 18 at the distal end of a redesignated positionable assembly 16a which replaces the positionable assembly 16 of the first embodiment. The inclusion of the rotary actuation system 150 provides additional control over the expanding or contracting size of the flexible and expandable mesh cage 18, whereby the operator does not rely solely on use of the stop 44 for limiting of the opening of the flexible and expandable mesh cage 18.

Facilitation of the rotary actuation system 150 into functionability with the first alternative embodiment is made by replacement of the strain relief 32, the connector 70, and the tubular extension 72 of the first embodiment by the multiple members of the rotary actuation system 150 having at least a rotary actuator 152, a spindle connector 154, a threaded tube 156 and a sleeve 158, shown generally in FIG. 7. In doing so, the rotary actuator 152, the spindle connector 154, and the greater majority of the threaded tube 156 join the manual actuator 58, the strain relief tube 56 and the sheath 54 to become a positionable assembly designated as positionable assembly 16a and as such the rotary actuator 152, the spindle connector 154 and the greater majority of the threaded tube 156 are common to the rotary actuation system 150 and the positionable assembly 16a.

Figure 10:
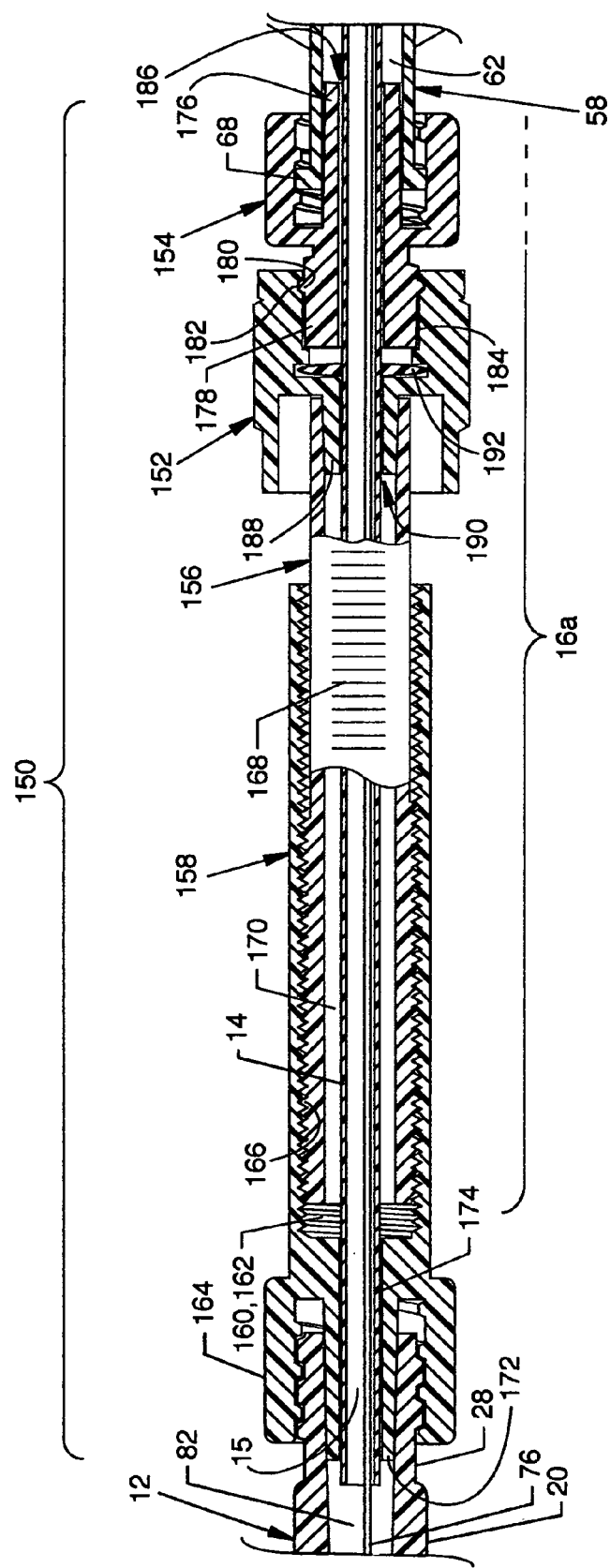
FIG. 10 is a cross section view of the rotary actuation system of the first alternative embodiment cross stream thrombectomy catheter with expandable cage along line 10-10 of FIG. 7.

FIG. 8 illustrates the elements of FIG. 7 in a partially cutaway view where major components and assemblies have been separated to facilitate description. More specifically, the sleeve 158 is shown disengaged from the threaded tube 156, the rotary actuator 152 and the spindle connector 154. As also shown in FIG. 10, the sleeve 158 is tubular in shape including an internally located passage 160 having threads 162 along a greater portion thereof. A connector 164 at the proximal end of the sleeve 158 is integral to and continuous with the structure of the sleeve 158 and secures the sleeve 158 over and about the threaded connection port 28 of the manifold 12. A portion of the length of the threaded tube 156 includes external threads 166, while the unthreaded portion includes incremental markings 168 therealong at a location distal to the threads 166, and additionally includes a passage 170, as shown in FIG. 10, for passage and accommodation of the catheter tube 14. The distal end of the threaded tube 156 permanently secures to the rotary actuator 152 as shown in FIG. 10. The rotary actuator 152 is rotatably attached to the spindle connector 154 and is free to be manually rotated about the longitudinal axis of each, whereby the threads 166 of the threaded tube 156 in engagement with the threads 162 of the sleeve 158 cooperatively and threadingly interact to cause displacement of the positionable assembly 16a with respect to the sleeve 158 along the catheter tube 14 to influence the shape of the flexible and expandable mesh cage 18.

Figure 9:
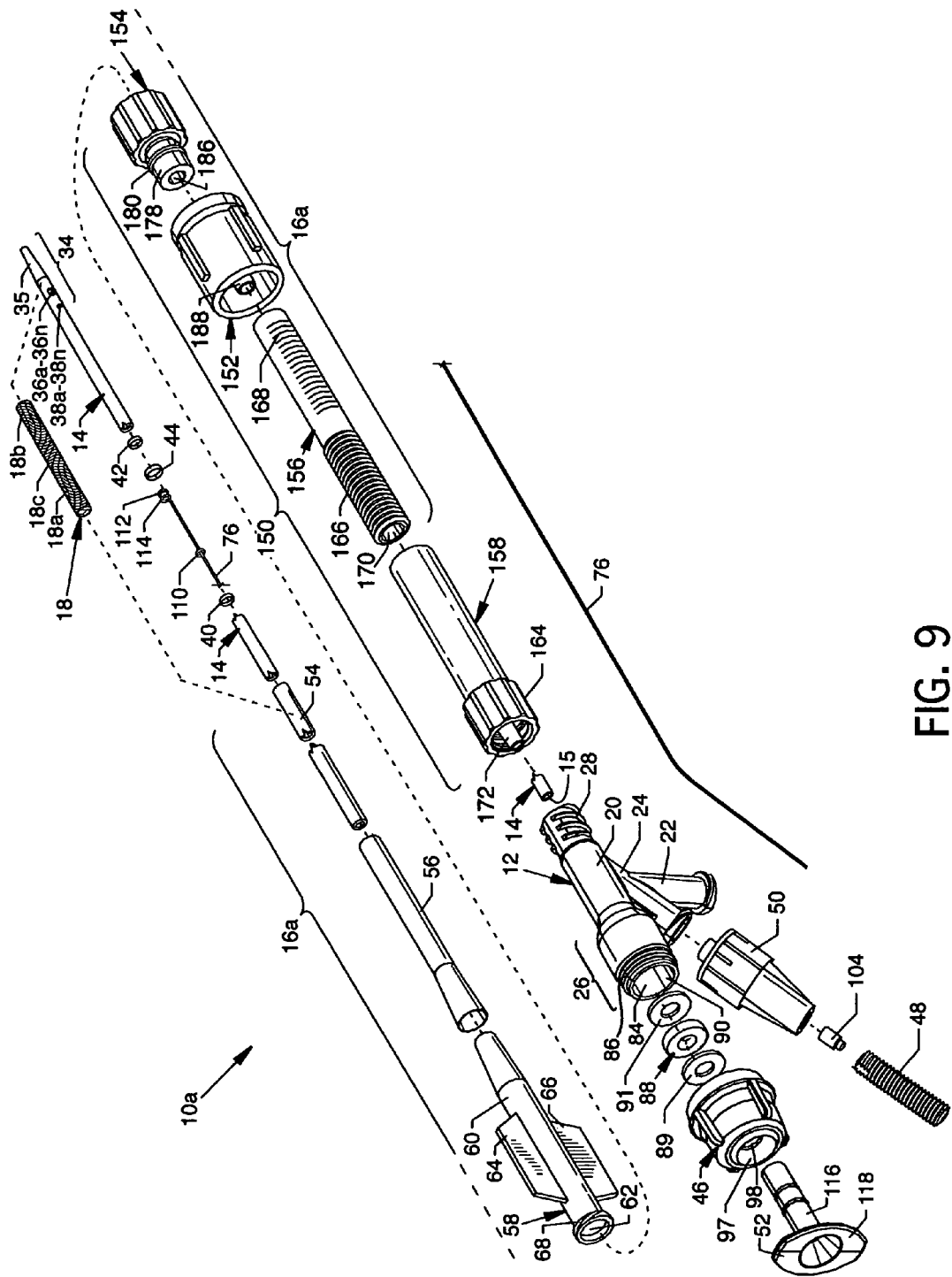
FIG. 9 is an exploded isometric view of the first alternative embodiment cross stream thrombectomy catheter with flexible and expandable cage.

FIG. 9 is an exploded isometric view of the cross stream thrombectomy catheter with flexible and expandable cage 10a, and FIG. 10 is a cross section view of the rotary actuation system 150 of the cross stream thrombectomy catheter with expandable cage 10a along line 10-10 of FIG. 7. With reference to FIGS. 9 and 10, the first alternative embodiment is further described with particular attention to the rotary actuation system 150. Illustrated in particular is the relationship of the components of the rotary actuation system 150, wherein certain components, such as the sleeve 158, are stationary with respect to other components of the rotary actuation system 150 and where other components, such as the threaded tube 156, the attached rotary actuator 152, and the spindle connector 154, are longitudinally positionable and translatory with respect to the stationary components of the rotary actuation system 150.

Stationary components of the rotary actuation system 150 involve the connector 164 of the sleeve 158 which engages the threaded connection port 28 of the manifold 12 wherein a cylindrical male fixture 172 of the connector 164 engages the tapered central passageway 82 of the manifold 12 to fixingly secure the sleeve 158 to the manifold 12. A bore 174 in the cylindrical male fixture 172 accommodates the catheter tube 14 which affixes therein, such as with adhesive or by other methods known in the art. The positionally fixed catheter tube 14 extends from the bore 174 distally to pass through a portion of the passage 160 having threads 162 and thence through the passage 170 of the threaded tube 156 and then through the rotary actuator 152 and the spindle connector 154 to distal paths along the manual actuator 58 and to locations distal thereto, as previously described.

Translatory and positionable components of the rotary actuation system 150 involve the threaded tube 156, the rotary actuator 152, and the spindle connector 154, collectively, employed to urge the manual actuator 58, the strain relief tube 56, and the sheath 54 along the catheter tube 14. The spindle connector 154 threadingly engages the threaded end 68 of the manual actuator 58 to cause a distally extending cylindrical male fixture 176 of the spindle connector 154 to sealingly engage the passage 62 of the manual actuator 58. A portion of the spindle connector 154 includes a proximally extending cylindrical spindle 178 including an integral ring 180 which engages an annular groove 182 located on the wall of a receptor cavity 184 of the rotary actuator 152 where such an arrangement allows rotary movement of the rotary actuator 152 about the cylindrical spindle 178 of the spindle connector 154. A continuous inner passage 186 extending through the cylindrical male fixture 176 and through the cylindrical spindle 178 is of sufficient diameter to freely and without significant friction pass over and about the fixed position catheter tube 14. The rotary actuator 152 includes a proximally extending cylindrical male fixture 188 having an inner passage 190 of sufficient diameter to freely and without significant friction pass over and about the fixed position catheter tube 14. A resilient seal washer 192 is also included within the rotary actuator 152 which seals about the catheter tube 14. The passage 170 of the threaded tube 156 accommodates the cylindrical male fixture 188 of the rotary actuator 152 and affixes thereto, such as with adhesive or by other methods known in the art.

Mode of Operation

The mode of operation of the cross stream thrombectomy catheter with a flexible and expandable cage 10a, the first alternative embodiment, is similar in a majority of functions to that of the cross stream thrombectomy catheter with a flexible and expandable cage 10, the major differences being the use of the rotary actuation system 150 in lieu of the previously described positioning of the manual actuator 58, where in operation of the first embodiment the operator manually grasps both the manifold 12 and the manual actuator 58 and positions one or the other or both components to cause the positionable assembly 16 to be slidingly positioned in a distal or proximal direction with respect to the manifold 12 and the attached catheter tube 14. During such positioning, the translatory distal end of catheter tube 14, upon which the proximal end 18a of the flexible and expandable mesh cage 18 is secured, is brought closer to the distal end 18b of the flexible and expandable mesh cage 18 which is in a fixed position about the tip 34. Such action causes forced outward deployment and expansion of the flexible and expandable mesh cage 18 where the central section 18c thereof expands radially to a rounded or bulbous conforming shape, whereby suitable intimate contact and engagement against the difficult to remove thrombus 124 occurs.

The use of the rotary actuation system 150 in the first alternative embodiment also provides for use of the flexible and expandable mesh cage 18, as previously described, but the method of actuation is more precise and better controlled. Preparation for use of the cross stream thrombectomy catheter with a flexible and expandable cage 10a including the rotary actuation system 150 is the same as for the first embodiment. Operation of the rotary actuation system 150 of the first alternative embodiment is accomplished by operating the rotary actuator 152 in a direction to cause rotation of the attached threaded tube 156 within the sleeve 158 while at the same time grasping either or both the manifold 12 or the manual actuator 58 to stabilize each against resultant rotation. As the rotary actuator 152 is operated in the proper direction to cause wanted deployment and expansion of the flexible and expandable mesh cage 18, the connected threaded tube 156 is correspondingly rotated, whereby the mutually engaged threads 166 of the threaded tube 156 and the threads 162 of the sleeve 158 force the threaded tube 156, the rotary actuator 152, the spindle connector 154, the manual actuator 58, the strain relief tube 56, and the sheath 54 distally along and about the catheter tube 14, whereby the distally directed distal end of the sheath 54 causes deployment and expansion of the flexible and expandable mesh cage 18, as previously described. The operator can readily observe and reference the incremental markings 168 on the threaded tube 156 with respect to the distal end of the sleeve 158 to determine the amount of travel of the threaded tube 156, and thus determine the amount of deployment and/or expansion of the flexible and expandable mesh cage 18. Any suitable type of calibration can be used as required where one could simply note the lineal displacement of the threaded tube or where the percentage of expansion could be indicated by appropriate markings or by other useful markings. Once the desired expansion of the flexible and expandable mesh cage 18 is achieved, the operator can cease adjusting the rotary actuator 152, whereby the expanded dimension of the flexible and expandable mesh cage 18 is maintained and locked by the interrelationship of the mutually engaged threads 166 of the threaded tube 156 and the threads 162 of the sleeve 158; i.e., the sheath 54 is held immovable and locked in position over and about the catheter tube 14. The cross stream thrombectomy catheter with a flexible and expandable cage 10a as a unit can then be unilaterally positioned to and fro or in rotary motion to cause abrasive contacting and removal of thrombus within the vasculature, as previously described. In both the cross stream thrombectomy catheter with a flexible and expandable cage 10 and the first alternative embodiment, the flexible and expandable mesh cage 18 can be collapsed and returned to a minimum profile by reversing the expansion and deployment processes in order to facilitate removal of the cross stream thrombectomy catheter with a flexible and expandable cage 10 and the cross stream thrombectomy catheter with a flexible and expandable cage 10a from the vasculature.

Although the flexible and expandable mesh cage 18 is shown at a location over and about the inflow orifices 36a-36n and the outflow orifices 38a-38n, other relationships and arrangements of components can also be utilized. One such arrangement includes locating the flexible and expandable mesh cage 18 proximal to the outflow orifices 38a-38n and another arrangement includes locating the flexible and expandable mesh cage 18 distal to the inflow orifices 36a-36n where in each arrangement the cross stream jets function separately from the flexible and expandable mesh cage 18. Further, either embodiment of the invention can be used solely as a cross stream thrombectomy catheter without enlisting the use of the flexible and expandable mesh cage 18.

Figure 11:
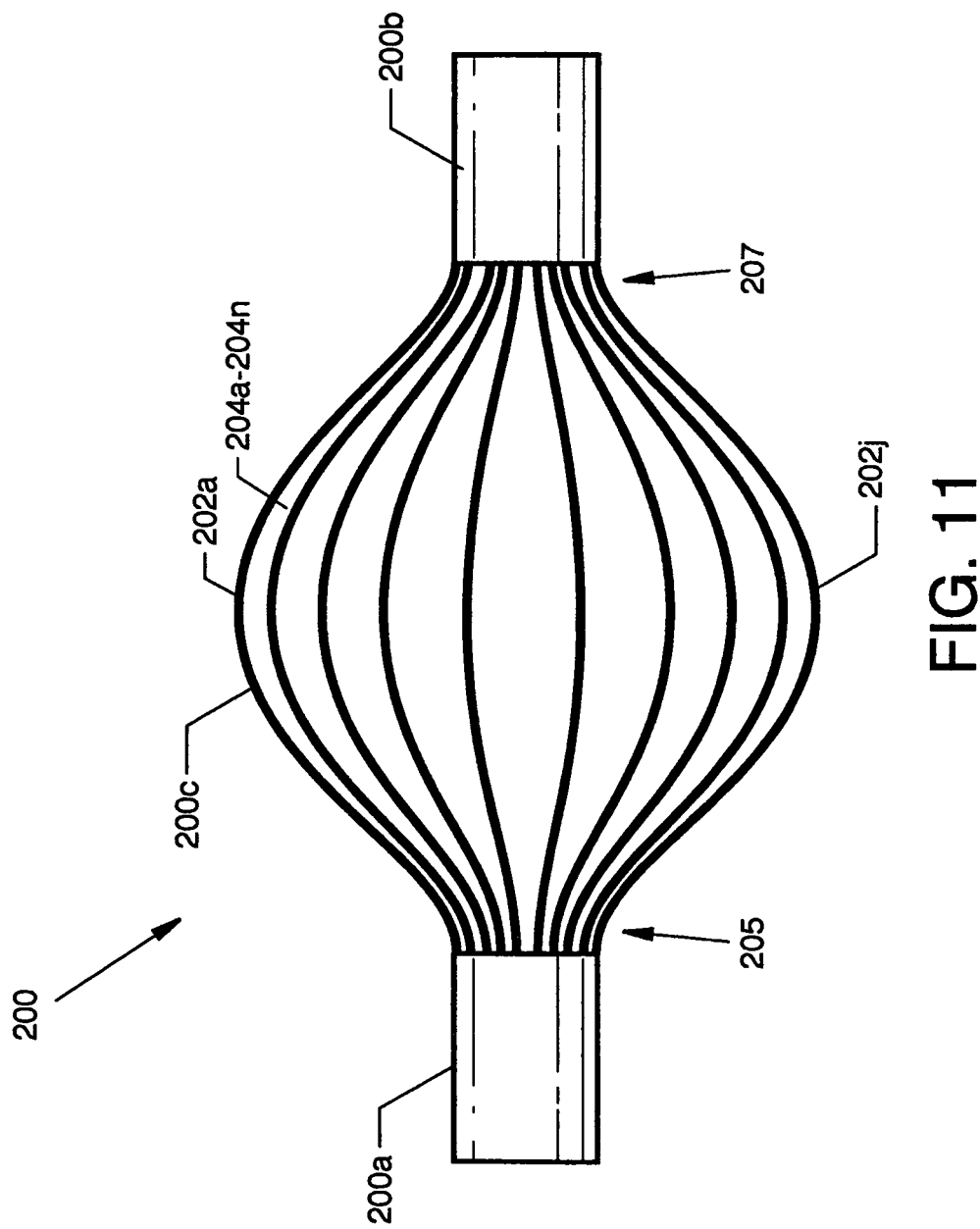
FIG. 11, a second alternative embodiment, is a side view of an expanded straight filament flexible and expandable cage.
Figure 17:
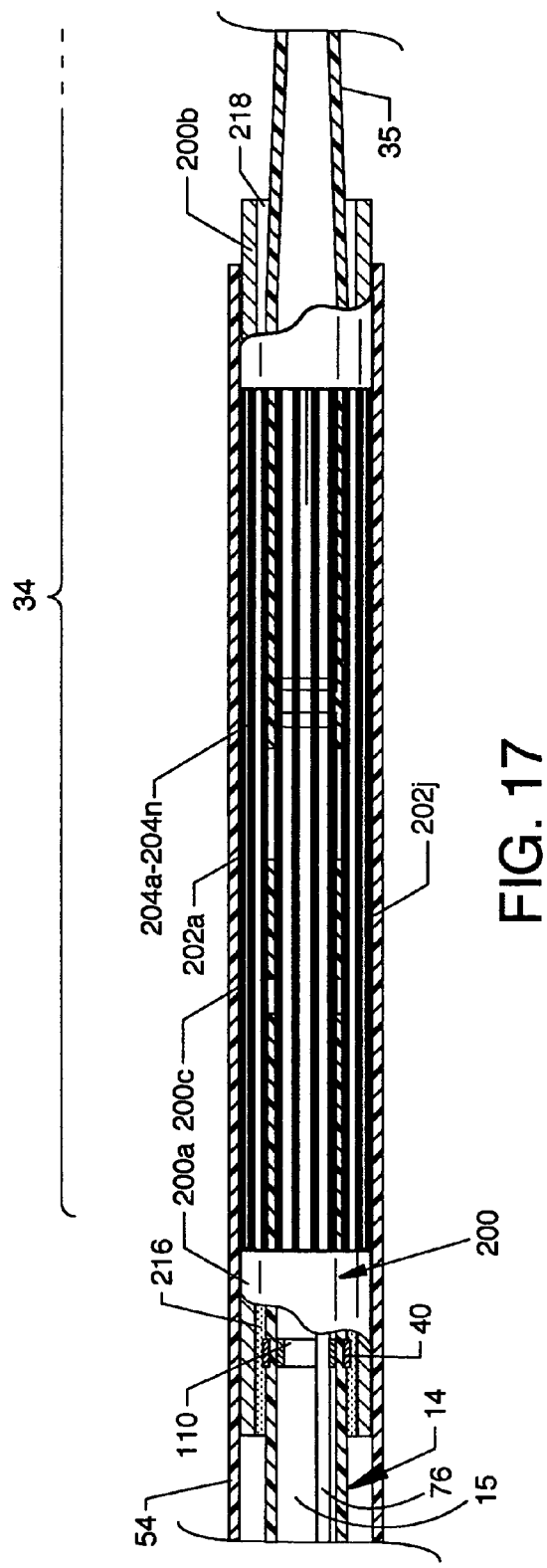
FIG. 17 is a view in partial cross section of the straight filament flexible and expandable cage constrained by the sheath; and, FIG. 18 is a view in partial cross section of the straight filament flexible and expandable cage and of the components shown in FIG. 17 where the sheath has been positioned proximally, whereby intimate and constraining contact between the sheath and the straight filaments no longer occurs.

FIG. 11, a second alternative embodiment, is a side view of an expanded straight filament flexible and expandable cage 200 which can be used as a device in lieu of the similarly attached flexible and expandable mesh cage 18 shown collapsed in FIGS. 1, 5c and 7, or which can be alternatively attached and incorporated as shown in FIGS. 17 and 18.

Figure 12:
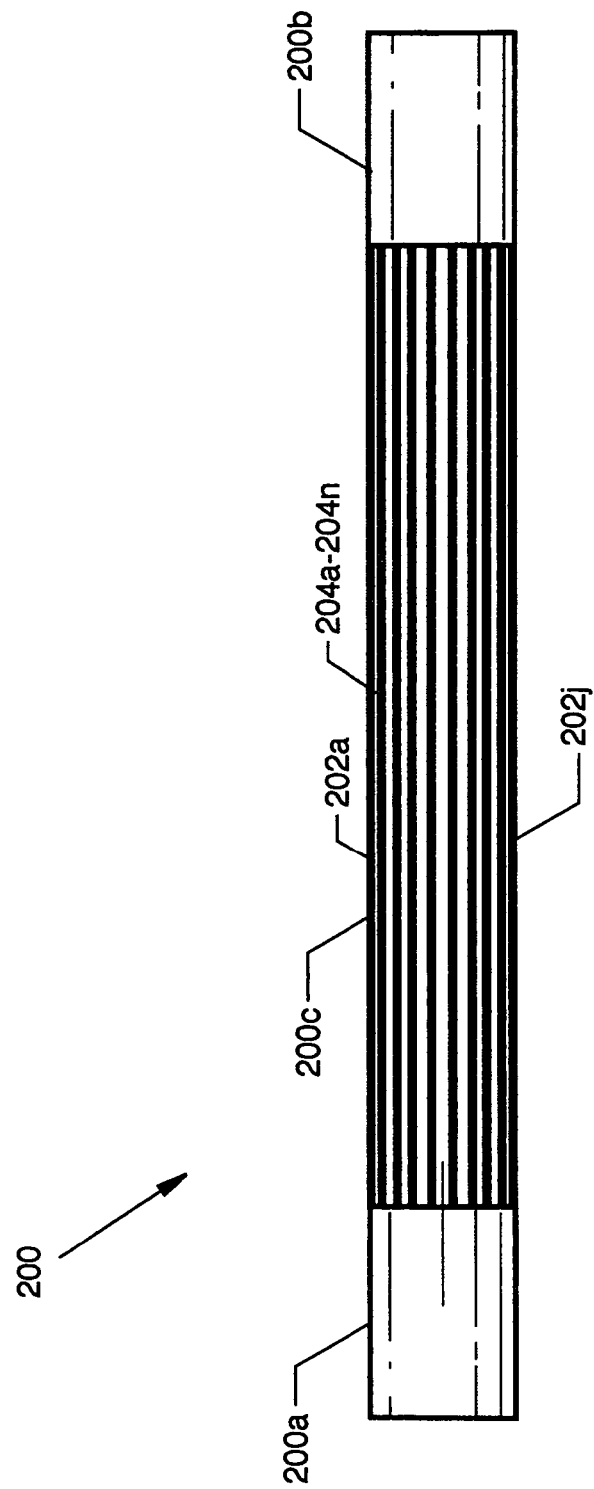
FIG. 12 is a side view of the straight filament flexible and expandable cage in a configuration such as it would appear when constrained by a sheath.

When used as a direct replacement for the expandable mesh cage 18, the straight filament flexible and expandable cage 200 can include a preformed collapsed shape heat set such as shown in FIG. 12, which minimizes the profile for insertion into the vasculature or into other devices such as, but not limited to, other catheters or sheaths.

In the latter case involving alternative attachment, the straight filament flexible and expandable cage 200 includes a heat set preformed expanded shape for use at the distal end of the combined sheath 54 and catheter tube 14 where the sheath 54 constrains members of the underlying straight filament flexible and expandable cage 200 (FIG. 17), wherein the sheath 54 is subsequently urged proximally to disengage from constrainment functions to allow expansion of the straight filament flexible and expandable cage 200 in an attempt to regain memory shape, as later described in detail. The term straight filament is best referenced to the compressed or restrained state of the straight filaments 202a-202n as shown in FIG. 12 where each filament is substantially straight. Upon encountering an uncompressed or unrestrained state, the filaments attempt to return to the expanded arcuate memory position. If any one filament is viewed in alignment with the centerline of the straight filament flexible and expandable cage 200, such viewing portrays a "straight"

filament. The straight filament flexible and expandable cage 200, preferably of nitinol, includes a proximal end 200a, a distal end 200b, each of uncut tubular nitinol material, and a central section 200c of straight filament (as opposed to spiral filament) tubular material consisting of a plurality of equally spaced straight filaments 202a-202n each being flexible, compressible and expandable and of one piece, and being continuous between and with the proximal end 200a and the distal end 200b and located in radial and equal spaced distribution bridging between the proximal end 200a and the distal end 200b of the straight filament flexible and expandable cage 200 and having spaces 204a-204n between the straight filaments 202a and 202n. In the expanded state, the straight filaments 202a-202n of the straight filament flexible and expandable cage 200 converge at both the proximal end 200a and the distal end 200b, as shown at 205 and 207, respectively. Correspondingly, the spaces 204a-204n are widely spaced in the central portion of the straight filament flexible and expandable cage 200 and are narrowly spaced at both the proximal end 200a and the distal end 200b, as shown at 205 and 207, respectively. The shapes of the straight filaments 202a-202n are heat set to maintain a preset outwardly bowed arcuate and curved shape. The straight filaments 202a-202n are covered by the sheath 54 which exerts constraining forces along and about the straight filaments 202a-202n of the straight filament flexible and expandable cage 200. Subsequent proximal movement of the sheath 54 allows expansion of the straight filament flexible and expandable cage 200 for use. When used instead of the flexible and expandable mesh cage 18, such as shown in FIGS. 1, 5c and 7, heat set shaping is not necessarily required. The illustration also shows the straight filament flexible and expandable cage 200 expandingly configured such as for use in the vasculature when substituted for the flexible and expandable mesh cage 18 where the sheath 54 is not incorporated for the purpose of constraint.

FIG. 12 is a side view of the straight filament flexible and expandable cage 200 in a configuration such as it would appear when constrained by the sheath 54 (not shown). Constrainment by the sheath 54 compressively forces the straight filaments 202a-202n inwardly to decrease the size of the spaces 204a-204n and also forces the straight filaments 202a-202n to maintain an elongated configuration, thereby and resultantly forcing the distal end 202b in a distal direction along the catheter tube 14 and away from the proximal end 200a. The illustration also shows the straight filament flexible and expandable cage 200 configured for insertion into the vasculature, such as when substituted for the flexible and expandable mesh cage 18 when the sheath 54 is not incorporated for the purpose of constraint.

Figure 13:
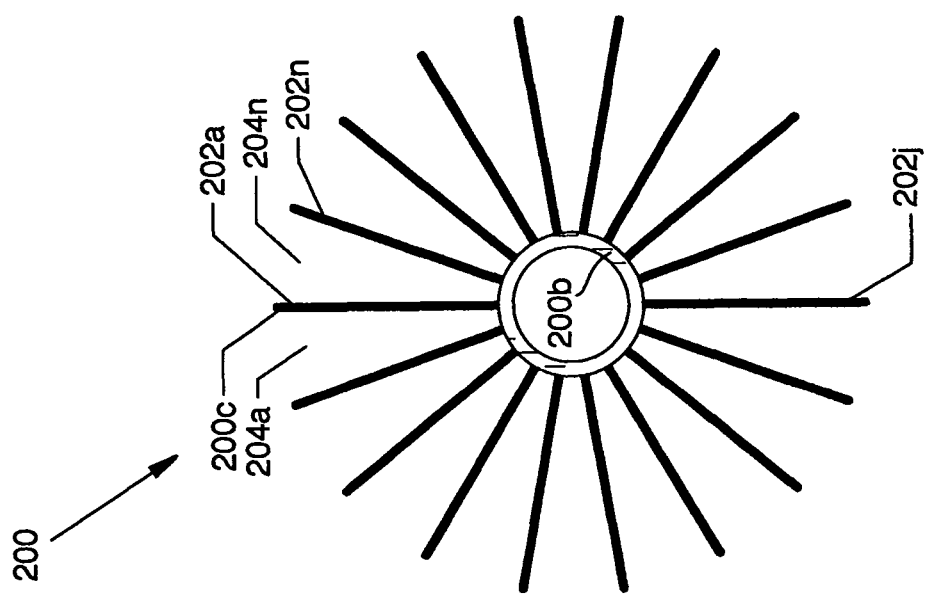
FIG. 13 is a distal end view of the expanded straight filament flexible and expandable cage.

FIG. 13 is a distal end view of the expanded straight filament flexible and expandable cage 200 showing the distribution and alignment of the straight filaments 202a-202n about the center of the straight filament flexible and expandable cage 200.

Figure 14:
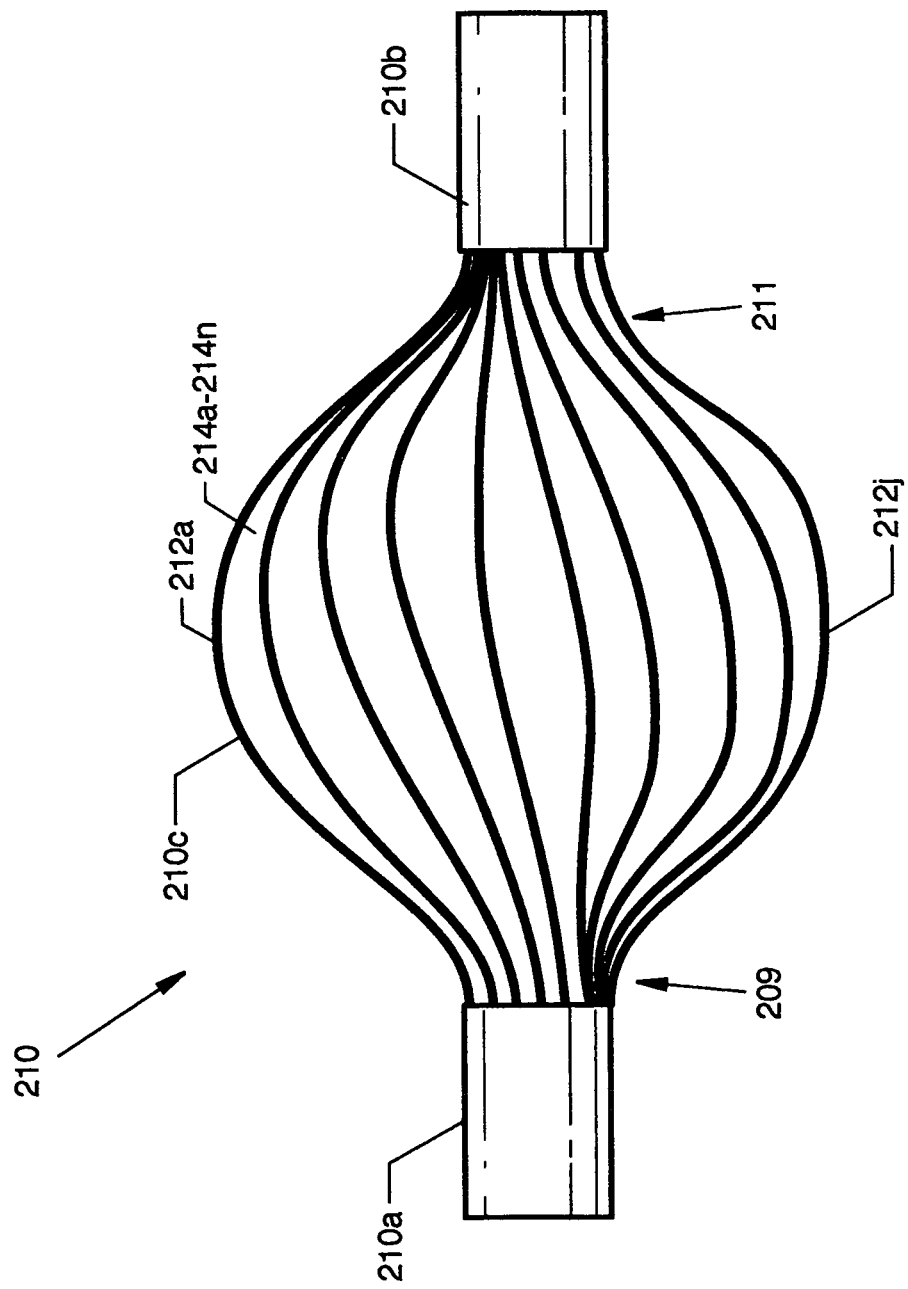
FIG. 14, a third alternative embodiment, is a side view of an expanded spiral filament flexible and expandable cage.

FIG. 14, a third alternative embodiment, is a side view of an expanded spiral filament flexible and expandable cage 210 which can be used as a device in lieu of the similarly attached flexible and expandable mesh cage 18 shown in FIGS. 1, 5c and 7, or which can be alternatively attached and incorporated in a similar manner such as shown in FIGS. 17 and 18.

Figure 15:
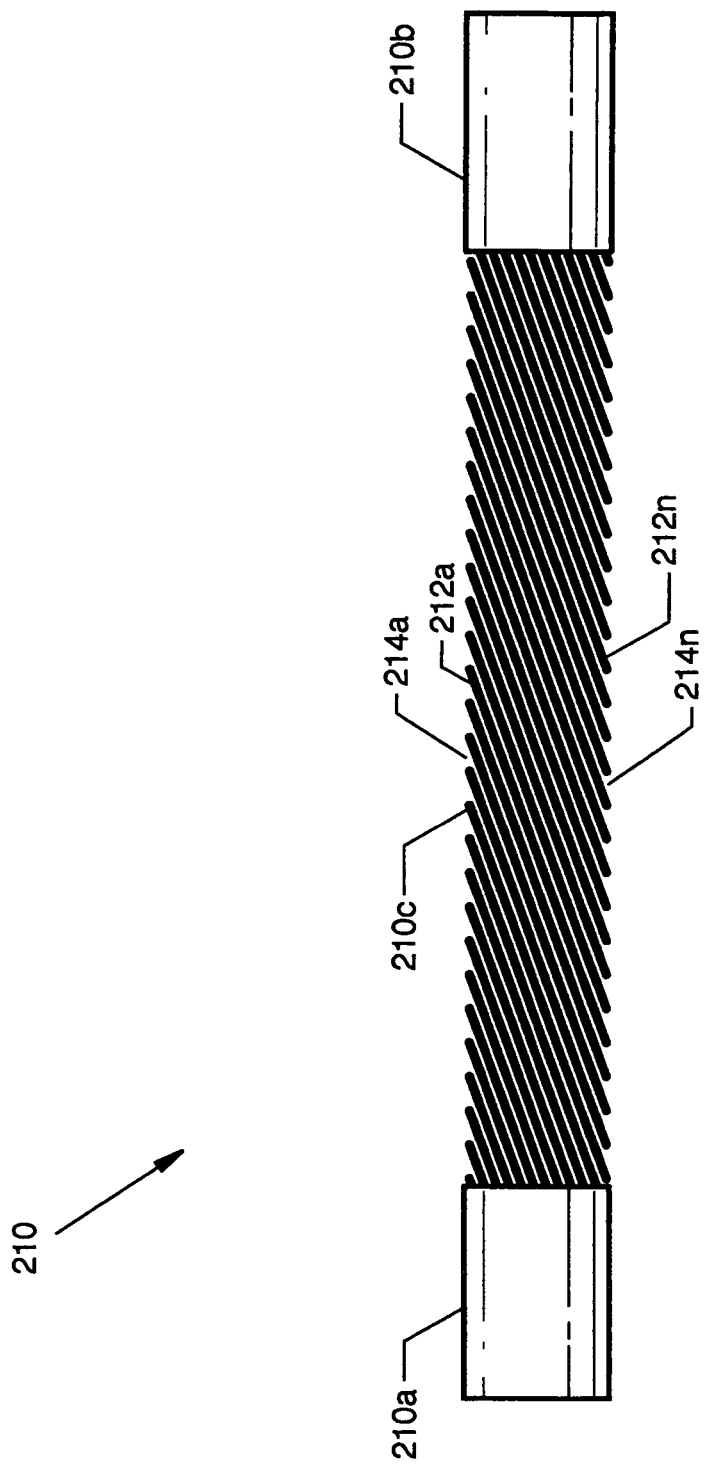
FIG. 15 is a side view of the spiral filament flexible and expandable cage in a configuration such as it would appear when constrained by a sheath.

When used as a direct replacement for the expandable mesh cage 18, the spiral filament flexible and expandable cage 210 can include a preformed collapsed shape heat set such as shown in FIG. 15 which minimizes the profile for insertion into the vasculature or into other devices such as, but not limited to, other catheters or sheaths.

In the latter case involving alternative attachment, the spiral filament flexible and expandable cage 210 includes a heat set preformed expanded shape for use at the distal end of the combined sheath 54 and catheter tube 14 where the sheath 54 constrains members of the underlying spiral filament flexible and expandable cage 210, wherein the sheath 54 is subsequently urged proximally to disengage from constrainment functions to allow expansion of the spiral filament flexible and expandable cage 210 in an attempt to regain memory shape, as later described in detail. The term spiral filament is best referenced to the compressed or restrained state of the spiral filaments 212a-212n, as shown in FIG. 15, where each filament portrays a spiral. Upon encountering an uncompressed or unrestrained state, the filaments attempt to return to the expanded spiral memory position where if any one of the filaments 212a-212n is viewed with respect to the centerline of the spiral filament flexible and expandable cage 210, such viewing portrays a "spiral" filament. The spiral filament flexible and expandable cage 210, preferably of nitinol, includes a proximal end 210a, a distal end 210b, each of uncut tubular material, and a central section 210c of spiral filament material consisting of a plurality of spirally shaped and spaced filaments 212a-212n each being flexible, compressible and expandable and of one piece, and being continuous between and with the proximal end 210a and the distal end 210b and located in radial and variable spaced distribution bridging between the proximal end 210a and the distal end 210b of the spiral filament flexible and expandable cage 210 and having variably spaced spaces 214a-214n between the spiral shaped filaments 212a-212n. For purposes of clarity, only the spiral shaped filaments 212a-212j nearest the viewer are shown to best illustrate the geometrical configuration and relationship of the spiral shaped filaments 212a-212n.

In the expanded state, the spiral filaments 212a-212n of the spiral filament flexible and expandable cage 210 converge at both the proximal end 210a and the distal end 200b, as shown at 209 and 211, respectively. Correspondingly, the spaces 214a-214n are widely spaced in the central portion of the spiral filament flexible and expandable cage 210 and are narrowly spaced at both the proximal end 210a and the distal end 210b, as shown at 209 and 211, respectively. The shapes of the filaments 212a-212n are heat set to maintain a preset outwardly bowed and twisting spiral shape. The filaments 212a-212n are covered by the sheath 54 which exerts constraining forces along and about the filaments 212a-212n of the spiral filament flexible and expandable cage 210. Subsequent proximal movement of the sheath 54 allows expansion of the spiral filament flexible and expandable cage 210 for use. When used instead of the flexible and expandable mesh cage 18, such as shown in FIGS. 1, 5c and 7, heat set shaping is not necessarily required. The illustration also shows the spiral filament flexible and expandable cage 210 expandingly configured, such as for use in the vasculature when substituted for the flexible and expandable mesh cage 18 where the sheath 54 is not incorporated for the purpose of constraint.

FIG. 15 is a side view of the spiral filament flexible and expandable cage 210 in a configuration such as it would appear when constrained by the sheath 54 (not shown). Constrainment by the sheath 54 compressively forces the spiral shaped filaments 212a-212n inwardly to decrease the size of the spaces 214a-214n and also forces the filaments 212a-212n to maintain an elongated configuration, thereby and resultantly forcing the distal end 210b in a distal direction along the catheter tube 14 and away from the proximal end 210a. The illustration also shows the spiral filament flexible and expandable cage 210 configured for insertion into the vasculature, such as when substituted for the flexible and expandable mesh cage 18 when the sheath 54 is not incorporated for the purpose of constraint.

Figure 16:
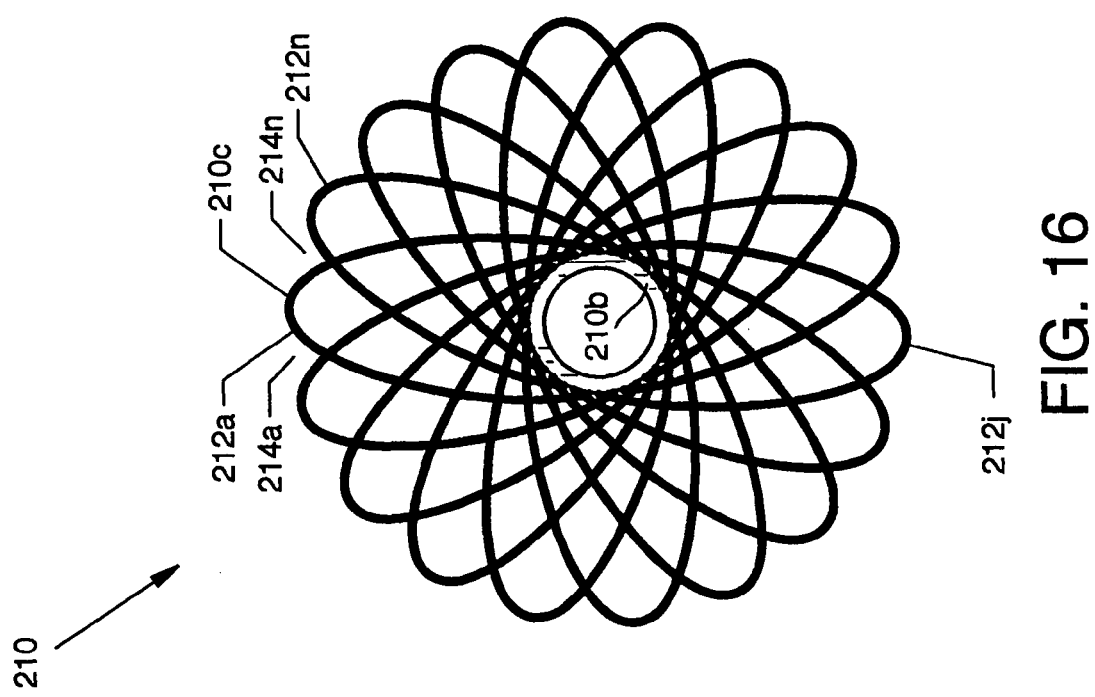
FIG. 16 is a distal end view of the expanded spiral filament flexible and expandable cage.

FIG. 16 is a distal end view of the expanded spiral filament flexible and expandable cage 210 showing the distribution and alignment of the spiral shaped filaments 212a-212n about the center of the spiral filament flexible and expandable cage 210.

FIG. 17 is a view in partial cross section of the straight filament flexible and expandable cage 200 constrained by the sheath 54 at the distal tip 34 in substitution for the positionable and expandable mesh cage 18 shown in the first embodiment and the first alternative embodiment of FIGS. 1 and 7, respectively. The proximal end 200a of the straight filament flexible and expandable cage 200 aligns over and about the catheter tube 14 at a location near the radiopaque band 40 and is affixed thereto by the use of an adhesive 216. The opposed distal end 200b of the straight filament flexible and expandable cage 200 aligns over and about the catheter tube 14 generally at a location distal to the plurality of inflow orifices 36a-36n and is not fixedly secured thereto, such as by adhesive, but is free to be urged or reactively positioned along and about the underlying catheter tube 14 in alignment with a substantially annular space 218 between the distal end 200b and the catheter tube 14.

FIG. 18 is a view in partial cross section of the straight filament flexible and expandable cage 200 and of the components shown in FIG. 17 where the sheath 54 has been positioned proximally, whereby intimate and constraining contact between the sheath 54 and the straight filaments 202a-202n no longer occurs. Such positioning allows the straight filaments 202a-202n to attempt to return to the memory position, thus allowing expansion and outward positioning of the straight filaments 202a-202n to attempt to return to the preset outwardly bowed arcuate and curved shape. As the straight filaments 202a-202n attempt to return to the memory position, the distal end 200b of the straight filament flexible and expandable cage 200 is urged proximally along and about the space 218 and the distal portion of the catheter tube 14 by preset memory forces of the expanding straight filaments 202a-202n.

Operation of the invention when using the straight filament flexible and expandable cage 200 is very much the same as previously described with reference to FIG. 6, but the straight filament flexible and expandable cage 200 is delivered to the thrombus site under the cover of the encompassing sheath 54 which is actuated proximally to deploy the straight filament flexible and expandable cage 200. Both to and fro linear motion and rotary motion of the straight filament flexible and expandable cage 200 and combinations thereof are incorporated into use. Use of the invention with the straight filament flexible and expandable cage 200 allows penetration of the thrombus by the straight filaments 202a-202n especially utilizing a linear ploughing penetration where the longitudinal profile, as shown in FIG. 13, of each of the straight filaments 202a-202n presents minimum frontal area for creation of thin paths through the thrombus, thereby easing to and fro linear penetration. Several to and fro reciprocating linear passes of the expanded straight filament flexible and expandable cage 200 followed by additional to and fro reciprocating linear passes where the expanded straight filament flexible and expandable cage 200 is rotatingly reoriented about its longitudinal axis at the ends of one or more linear passes can serve to plough several and multiple different paths through the thrombus, thereby weakening the thrombus structure. Rotary motion of the expanded straight filament flexible and expandable cage 200 can be incorporated with intimate contact to abrade, grate, scrape, or otherwise loosen and disturb or otherwise dislodge difficult to remove thrombus where the expanded straight filament flexible and expandable cage 200 is positioned in the thrombus and rotated about its longitudinal axis. Rotary motion of the expanded straight filament flexible and expandable cage 200 can be incorporated by itself or in combination with multiple reoriented to and fro linear reciprocating passes thereof or also by combining rotary motion and to and fro reciprocating non-linear motion (simultaneous push/pull and twist) where such intimate contact actions are incorporated to abrade, grate, scrape, or otherwise loosen and dislodge difficult to remove thrombus. Loosened thrombus can be acted upon by cross stream jets for entrainment for maceration and/or for evacuation through the catheter tube. During operation of a thrombectomy catheter having a straight filament flexible and expandable cage 200 in a to and fro and/or a rotary motion to cause the deployed straight filament flexible and expandable cage 200 to frictionally abrade, grate, scrape, or otherwise loosen and dislodge difficult to remove thrombus, the particles of such thrombus can be engaged in the spaces 204a-204n, especially at the narrowed spaces 204a-204n formed by the converging straight filaments 202a-202n, such as shown at 205 and 207. Further and more emphatic frictional engagement of thrombus particles between the straight filaments 202a-202n can occur as the spaces 204a-204n are forced to close during collapsing of the straight filament flexible and expandable cage 200 by the constraining action of the distally actuated sheath 54. Additionally, when the straight filaments 202a-202n are compressed by the sheath 54, any stray particulate which is not exhausted through the catheter tube 14 and in close proximity about the region of the catheter tube 14 surrounded by the straight filaments 202a-202n can be contained in the inner space formed by the closely spaced and compressed straight filaments 202a-202n which assume a cylindrical shape. Thrombus particles which are capturingly engaged by the collapsed straight filament flexible and expandable cage 200 are removed from the vasculature when the catheter tube 14 and the positionable assembly 16 are removed from the vasculature. When the straight filament flexible and expandable cage 200 is collapsed and retracted, the tubular catheter 14 can be maneuvered from the former thrombus site and from the vasculature.

Operation of the invention when using the spiral filament flexible and expandable cage 210 is very much the same as previously described with relation to FIG. 6 concerning the flexible and expandable mesh cage 18. As with the straight filament flexible and expandable cage 200, the spiral filament flexible and expandable cage 210 is delivered to the thrombus site under the cover of the encompassing sheath 54 which is thereafter actuated proximally to deploy the spiral filament flexible and expandable cage 210.

The spiral filament flexible and expandable cage 210 can be used instead of the straight filament flexible and expandable cage 200 where the spiral filament flexible and expandable cage 210 is mounted in a similar fashion, as just described above with reference to FIGS. 17 and 18. The spiral filament flexible and expandable cage 210 is delivered to the thrombus site under the cover of the encompassing sheath 54 which is then actuated proximally to deploy and expose the spiral filament flexible and expandable cage 210 within the vasculature. The spiral filament flexible and expandable cage 210 can be incorporated into use with to and fro linear motion, with rotary motion, or with a combination of to and fro linear motion and rotary motion. During to and fro actuation of the spiral filament flexible and expandable cage 210, a wide total contact circular path is made by the overlapping profile of the plurality of spiral filaments 212a-212n (see FIG. 16) instead of multiple thin paths such as are made by the straight filaments 202a-202n of the straight filament flexible and expandable cage 200. Therefore, use of the spiral filament flexible and expandable cage 210 can hasten the thrombectomy process. Rotary motion can also be effective using intimate contact to abrade, grate, scrape, or otherwise loosen and dislodge difficult to remove thrombus. An additional benefit is that the rotating spiral filaments 212a-212n can also slice or peel thrombus from the main thrombus buildup due to the angular incidence of the spiral filaments 212a-212n with the thrombus buildup. Another benefit of the spiral filament flexible and expandable cage 210 is that, with reference to profile, contact is made along multiple spiral broadly encompassing regions as opposed to contact along thin multiple straight paths using straight filaments where straight filaments could fall into the thin ploughed paths for temporary captured hindrance to further rotation. During operation of a thrombectomy catheter having a spiral filament flexible and expandable cage 210 in a to and fro and/or a rotary motion or other suitable motion to cause the deployed spiral filament flexible and expandable cage 210 to frictionally abrade, grate, scrape, or otherwise loosen and dislodge difficult to remove thrombus, the particles of such thrombus can be engaged in the spaces 214a-214n, especially at the narrowed spaces 214a-214n formed by the converging spiral filaments 212a-212n, such as shown at 209 and 211. Further and more emphatic frictional engagement of thrombus particles between the spiral filaments 212a-212n can occur as the spaces 214a-214n are forced to close during collapsing of the spiral filament flexible and expandable cage 210 by the constraining action of the distally actuated sheath 54. Additionally, when the spiral filaments 212a-212n are compressed by the sheath 54, any stray particulate which is not exhausted through the catheter tube 14 and in close proximity about the region of the catheter tube 14 surrounded by the spiral filaments 212a-212n can be contained in the inner space formed by the closely spaced and compressed spiral filaments 212a-212n which assume a cylindrical shape. Thrombus particles which are capturingly engaged by the collapsed spiral filament flexible and expandable cage 210 are removed from the vasculature when the catheter tube 14 and the positionable assembly 16 are removed from the vasculature.

Multiple arrangements, combinations, and uses of component members can be utilized. For instance, the first embodiment of the cross stream thrombectomy catheter with a flexible and expandable cage 10 (FIG. 1) and the first alternative embodiment of the cross stream thrombectomy catheter with a flexible and expandable cage 10a (FIG. 7) are shown featuring the flexible and expandable mesh cage 18 where the cross stream thrombectomy catheter with flexible and expandable cage 10 includes the sheath 54 which is simply and manually actuated to cause expanding deployment of the flexible and expandable mesh cage 18, and the first alternative embodiment features the sheath 54 which is actuated incrementally and precisely by use of the rotary actuation system 150 to cause expanding deployment of the flexible and expandable mesh cage 18. Each of the above embodiments demonstrates the use of a flexible and expandable mesh cage 18 being deployed at the distal end of the sheath 54 in different manners.

Use of the second alternative embodiment (straight filament flexible and expandable cage 200) or the third alternative embodiment (spiral filament flexible and expandable cage 210) at the distal end of the sheath 54 of the first embodiment (cross stream thrombectomy catheter with flexible and expandable cage 10), and use of the second alternative embodiment (straight filament flexible and expandable cage 200) or the third alternative embodiment (spiral filament flexible and expandable cage 210) at the distal end of the sheath 54 of the first alternative embodiment (cross stream thrombectomy catheter with flexible and expandable cage 10a) are other uses and examples of various arrangements, combinations, and uses of components of the first embodiment, wherein such uses can incorporate the sheath 54 to house or reveal or to collapse and capture the straight or spiral filament flexible and expandable cages 200 and 210. The flexible and expandable mesh cage 18 could also be mounted to the catheter where the proximal end is secured thereto and where the distal end is free to slide along and about the distal end of the catheter 14, much in the same manner as shown in the second alternative embodiment, involving the use of the sheath 54 to house or reveal the flexible and expandable mesh cage 18.

Various modifications can be made to the present invention without departing from the apparent scope hereof.

It is claimed:
1. A thrombectomy catheter comprising:
a catheter tube having a distal end and a proximal end;
a porous cage distally located on the catheter tube, the porous cage characterized as capable of radial expansion and radial contraction;
a proximally located control means regulating radial expansion and radial contraction of the porous cage;
at least one outflow orifice and at least one inflow orifice situated on the catheter tube adjacent the distal end of the catheter, wherein the at least one outflow orifice and the at least one inflow orifice are located within the porous cage;
a manifold connected to the proximal end of the catheter tube, the manifold providing for connection to pressurizing and/or evacuation equipment and providing fluid communication with the at least one outflow orifice and the at least one inflow orifice, such that a cross stream jet may be established between the at least one outflow orifice and the at least one inflow orifice, and the at least one outflow orifice is configured to direct the cross stream jet radially out toward the porous cage; and
a sheath slidably coupled over the catheter tube, the sheath is movable between a cage covering position and a cage exposing position, in the cage covering position the sheath covers the porous cage, in the cage exposing position the sheath uncovers the porous cage;
wherein the porous cage has a distal end and a proximal end;
wherein the distal end of the porous cage is fixed to the catheter tube and the proximal end of the porous cage is free floating and movable along and over the catheter tube; and
wherein the proximally located control means includes a manual actuator longitudinally slidable over a proximally located segment of the catheter tube, the manual actuator operating the sheath extending distally over the catheter tube and connecting to the free floating and movable proximal end of the porous cage.

2. The thrombectomy catheter of claim 1, wherein the porous cage includes nitinol.

3. The thrombectomy catheter of claim 1, wherein the porous cage is a mesh cage.

4. The thrombectomy catheter of claim 3, wherein the porous mesh cage is a porous woven mesh cage.

5. The thrombectomy catheter of claim 1, wherein the porous cage includes a plurality of flexible filaments.

6. The thrombectomy catheter of claim 1, wherein the proximally located control means further includes indicia for aid in selecting a desired degree of expansion of the porous cage.

7. The thrombectomy catheter of claim 1, wherein the plurality of filaments are spiral.

8. The thrombectomy catheter of claim 1, wherein the porous cage, when contracted, includes a plurality of straight filaments, the plurality of straight filaments arranged in a longitudinally oriented parallel manner such that the plurality of straight filaments together define a generally tubular configuration.

9. The thrombectomy catheter of claim 8, wherein the straight filaments of the porous cage are formed of nitinol.

10. The thrombectomy catheter of claim 9, wherein the straight nitinol filaments have a preset memory shape, which preset memory shape predisposes the straight nitinol filaments to assume an arcuate shape and the predisposed arcuate shape of each of the straight nitinol filaments of the plurality being directed such that the porous cage is predisposed to radially expand.

11. The thrombectomy catheter of claim 10, wherein the preset memory shape is a heat set memory shape.

12. A thrombectomy catheter comprising:
a catheter tube having a catheter distal end portion and a catheter proximal end portion, the catheter tube includes a catheter lumen extending from the catheter distal end portion to the catheter proximal end portion;
a thrombectomy assembly comprising:
a high pressure tube extending from a high pressure tube proximal end portion to a high pressure tube distal end portion, at least a portion of the high pressure tube extends through the catheter tube,
a fluid jet emanator coupled with the high pressure tube distal end portion, the fluid jet emanator is configured to provide one or more fluid jet streams directed proximally through the catheter lumen toward the high pressure tube proximal end portion, the catheter tube surrounds and covers the fluid jet emanator, and the catheter tube is interposed between the fluid jet emanator and the porous cage, and
a porous cage adjacent the high pressure tube distal end portion, a cage proximal portion is coupled with the high pressure tube distal end portion, and the fluid jet emanator is positioned within the porous cage; and
a sheath slidably coupled along the thrombectomy assembly, the sheath is movable from a cage covering position to a cage exposing position, and the porous cage radially expands into an expanded cage configuration from a stored cage configuration according to movement of the sheath between the cage covering and exposing positions, and the fluid jet emanator and the porous cage are positioned outside of the sheath with the sheath in the cage exposing position; and
wherein the radial expansion and contraction of the porous cage is controlled by a proximal control coupled with the sheath.

13. The thrombectomy catheter of claim 12, wherein the porous cage includes nitinol.

14. The thrombectomy catheter of claim 12, wherein the porous cage is a mesh cage.

15. The thrombectomy catheter of claim 14, wherein the porous mesh cage is a porous woven mesh cage.

16. The thrombectomy catheter of claim 12, wherein the porous cage includes a plurality of flexible filaments.

17. The thrombectomy catheter of claim 12, wherein the plurality of filaments are spiral.

18. The thrombectomy catheter of claim 12, wherein the proximally located control means further includes indicia for aid in selecting a desired degree of expansion of the porous cage.

19. A thrombectomy catheter comprising:
a catheter tube having a catheter distal end portion and a catheter proximal end portion, the catheter tube includes a catheter lumen extending from the catheter distal end portion to the catheter proximal end portion;
a thrombectomy assembly comprising:
a high pressure tube extending from a high pressure tube proximal end portion to a high pressure tube distal end portion, at least a portion of the high pressure tube extends through the catheter tube,
a fluid jet emanator coupled with the high pressure tube distal end portion, the fluid jet emanator is configured to provide one or more fluid jet streams directed proximally through the catheter lumen toward the high pressure tube proximal end portion, the catheter tube surrounds and covers the fluid jet emanator, and the catheter tube is interposed between the fluid jet emanator and the porous cage, and
a porous cage adjacent the high pressure tube distal end portion, a cage proximal portion is coupled with the high pressure tube distal end portion, and the fluid jet emanator is positioned within the porous cage; and
a sheath slidably coupled along the thrombectomy assembly, the sheath is movable from a cage covering position to a cage exposing position, and the porous cage radially expands into an expanded cage configuration from a stored cage configuration according to movement of the sheath between the cage covering and exposing positions, and the fluid jet emanator and the porous cage are positioned outside of the sheath with the sheath in the cage exposing position; and
wherein the porous cage is biased and predisposed to radial expansion, and movement of the sheath to the exposing position allows the porous cage to expand according to the bias.

20. The thrombectomy catheter of claim 19, wherein the plurality of filaments are spiral.

21. The thrombectomy catheter of claim 19, wherein the porous cage includes nitinol.

22. The thrombectomy catheter of claim 19, wherein the porous cage is a mesh cage.

23. The thrombectomy catheter of claim 22, wherein the porous mesh cage is a porous woven mesh cage.

24. The thrombectomy catheter of claim 19, wherein the porous cage includes a plurality of flexible filaments.

25. The thrombectomy catheter of claim 19, wherein the proximally located control means further includes indicia for aid in selecting a desired degree of expansion of the porous cage.

26. A thrombectomy catheter comprising:
a catheter tube having a catheter distal end portion and a catheter proximal end portion, the catheter tube includes a catheter lumen extending from the catheter distal end portion to the catheter proximal end portion;
a thrombectomy assembly comprising:
a high pressure tube extending from a high pressure tube proximal end portion to a high pressure tube distal end portion, at least a portion of the high pressure tube extends through the catheter tube,
a fluid jet emanator coupled with the high pressure tube distal end portion, the fluid jet emanator is configured to provide one or more fluid jet streams directed proximally through the catheter lumen toward the high pressure tube proximal end portion, the catheter tube surrounds and covers the fluid jet emanator, and the catheter tube is interposed between the fluid jet emanator and the porous cage, and a porous cage adjacent the high pressure tube distal end portion, a cage proximal portion is coupled with the high pressure tube distal end portion, and the fluid jet emanator is positioned within the porous cage; and a sheath slidably coupled along the thrombectomy assembly, the sheath is movable from a cage covering position to a cage exposing position, and the porous cage radially expands into an expanded cage configuration from a stored cage configuration according to movement of the sheath between the cage covering and exposing positions, and the fluid jet emanator and the porous cage are positioned outside of the sheath with the sheath in the cage exposing position; and wherein the cage proximal portion is coupled with the catheter distal end portion, and the cage distal portion is free floating and slidably coupled along the catheter distal end portion.

27. The thrombectomy catheter of claim 26, wherein the porous cage includes nitinol.

28. The thrombectomy catheter of claim 26, wherein the porous cage is a mesh cage.

29. The thrombectomy catheter of claim 26, wherein the porous mesh cage is a porous woven mesh cage.

30. The thrombectomy catheter of claim 29, wherein the porous cage includes a plurality of flexible filaments.

31. The thrombectomy catheter of claim 26, wherein the plurality of filaments are spiral.

32. The thrombectomy catheter of claim 26, wherein the proximally located control means further includes indicia for aid in selecting a desired degree of expansion of the porous cage.

33. A thrombectomy catheter comprising:

a catheter tube having a catheter distal end portion and a catheter proximal end portion, the catheter tube includes a catheter lumen extending from the catheter distal end portion to the catheter proximal end portion;

a thrombectomy assembly comprising:

a high pressure tube extending from a high pressure tube proximal end portion to a high pressure tube distal end portion, at least a portion of the high pressure tube extends through the catheter tube, a fluid jet emanator coupled with the high pressure tube distal end portion, the fluid jet emanator is configured to provide one or more fluid jet streams directed proximally through the catheter lumen toward the high pressure tube proximal end portion, the catheter tube surrounds and covers the fluid jet emanator, and the catheter tube is interposed between the fluid jet emanator and the porous cage, and a porous cage adjacent the high pressure tube distal end portion, a cage proximal portion is coupled with the high pressure tube distal end portion, and the fluid jet emanator is positioned within the porous cage; and a sheath slidably coupled along the thrombectomy assembly, the sheath is movable from a cage covering position to a cage exposing position, and the porous cage radially expands into an expanded cage configuration from a stored cage configuration according to movement of the sheath between the cage covering and exposing positions, and the fluid jet emanator and the porous cage are positioned outside of the sheath with the sheath in the cage exposing position; and wherein the catheter tube includes at least one outflow orifice and at least one inflow orifice situated on the catheter tube adjacent the distal end of the catheter, wherein the at least one outflow orifice and the at least one inflow orifice are interposed between the fluid jet emanator and the porous cage.

34. The thrombectomy catheter of claim 33, wherein the porous cage includes nitinol.

35. The thrombectomy catheter of claim 33, wherein the porous cage is a mesh cage.

36. The thrombectomy catheter of claim 33, wherein the porous mesh cage is a porous woven mesh cage.

37. The thrombectomy catheter of claim 36, wherein the porous cage includes a plurality of flexible filaments.

38. The thrombectomy catheter of claim 33, wherein the plurality of filaments are spiral.

39. The thrombectomy catheter of claim 33, wherein the proximally located control means further includes indicia for aid in selecting a desired degree of expansion of the porous cage.

* * * * *

UNITED STATES PATENT AND TRADEMARK OFFICE
CERTIFICATE OF CORRECTION

PATENT NO. : 8,475,487 B2  
APPLICATION NO. : 11/101224  
DATED : July 2, 2013  
INVENTOR(S) : Bonnette et al.

Page 1 of 1

It is certified that error appears in the above-identified patent and that said Letters Patent is hereby corrected as shown below:

IN THE SPECIFICATION:

In Column 8, Line 25, delete "cavity body 20" and insert -- cavity body 26 --, therefor.

In Column 11, Line 32, delete "boa," and insert -- 10a, --, therefor.

Signed and Sealed this  
First Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO. : 8,475,487 B2  
APPLICATION NO. : 11/101224  
DATED : July 2, 2013  
INVENTOR(S) : Bonnette et al.

It is certified that error appears in the above-identified patent and that said Letters Patent is hereby corrected as shown below:

IN THE CLAIMS:

In Column 20, Line 65, Claim 4, delete "porous mesh cage is a porous woven mesh cage." and insert -- mesh cage is a porous woven mesh cage. --, therefor.

In Column 21, Line 5, Claim 6, delete "claim 1," and insert -- claim 5, --, therefor.

In Column 21, Line 6, Claim 6, delete "of filaments," and insert -- of flexible filaments, --, therefor.

In Column 21, Line 41, Claim 12, delete "the," and insert -- a, --, therefor.

In Column 21, Line 42, Claim 12, delete "a porous cage adjacent," and insert -- the porous cage is adjacent, --, therefor.

In Column 21, Lines 51-52, Claim 12, delete "covering and exposing positions," and insert -- covering position and the cage exposing position, --, therefor.

Signed and Sealed this  
Twenty-ninth Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO.        : 8,475,487 B2                                  Page 1 of 2
APPLICATION NO.   : 11/101224
DATED             : July 2, 2013
INVENTOR(S)       : Bonnette et al.

It is certified that error appears in the above-identified patent and that said Letters Patent is hereby corrected as shown below:

IN THE CLAIMS:

In Claim 15, Column 21, Line 63, delete "porous mesh cage is a porous woven mesh cage." and insert -- mesh cage is a porous woven mesh cage. --, therefor.

In Claim 17, Column 21, Line 66, delete "claim 12," and insert -- claim 16, --, therefor.

In Claim 17, Column 21, Line 67, delete "plurality of filaments," and insert -- plurality of flexible filaments, --, therefor.

In Claim 19, Column 22, Line 22, delete "the," and insert -- a, --, therefor.

In Claim 19, Column 22, Line 23, delete "a porous cage adjacent," and insert -- the porous cage is adjacent, --, therefor.

In Claim 19, Column 22, Lines 28-29, delete "covering and exposing positions," and insert -- covering position and the cage exposing position --, therefor.

In Claim 20, Column 22, Line 39, delete "claim 19," and insert -- claim 24, --, therefor.

In Claim 20, Column 22, Line 40, delete "plurality of filaments," and insert -- plurality of flexible filaments, --, therefor.

In Claim 23, Column 22, Line 46, delete "porous mesh cage is a porous woven mesh cage." and insert -- mesh cage is a porous woven mesh cage. --, therefor.

In Claim 26, Column 23, Line 3, delete "the," and insert -- a, --, therefor.

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,475,487 B2

In Claim 26, Column 23, Line 4, delete "a porous cage adjacent," and insert -- the porous cage is adjacent, --, therefor.

In Claim 26, Column 23, Lines 9-10, delete "covering and exposing positions," and insert -- covering position and the cage exposing position --, therefor.

In Claim 29, Column 23, Line 26, delete "porous mesh cage is a porous woven mesh cage." and insert -- mesh cage is a porous woven mesh cage. --, therefor.

In Claim 31, Column 23, Line 30, delete "claim 26," and insert -- claim 30, --, therefor.

In Claim 31, Column 23, Line 31, delete "plurality of filaments," and insert -- plurality of flexible filaments, --, therefor.

In Claim 34, Column 24, Line 10, delete "the," and insert -- a, --, therefor.

In Claim 34, Column 24, Line 11, delete "a porous cage adjacent," and insert -- the porous cage is adjacent, --, therefor.

In Claim 34, Column 24, Lines 15-16, delete "covering and exposing positions," and insert -- covering position and the cage exposing position --, therefor.

In Claim 36, Column 24, Line 33, delete "porous mesh cage is a porous woven mesh cage." and insert -- mesh cage is a porous woven mesh cage. --, therefor.

In Claim 38, Column 24, Line 36, delete "claim 33," and insert -- claim 37, --, therefor.

In Claim 38, Column 24, Line 37, delete "plurality of filaments," and insert -- plurality of flexible filaments, --, therefor.